(12) United States Patent
Pless et al.

(10) Patent No.: US 9,232,903 B2
(45) Date of Patent: *Jan. 12, 2016

(54) SYSTEMS AND METHODS FOR INTERACTING WITH AN IMPLANTABLE MEDICAL DEVICE

(71) Applicant: NeuroPace, Inc., Mountain View, CA (US)

(72) Inventors: Benjamin D Pless, Atherton, CA (US); David R. Fischell, Larchmont, NY (US); Barbara Gibb, Foster City, CA (US); Lisa Guzzo, Menlo Park, CA (US); Adrian R. M. Upton, Dundas (CA)

(73) Assignee: NeuroPace, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,486

(22) Filed: Jul. 7, 2014

(65) Prior Publication Data

US 2014/0323902 A1 Oct. 30, 2014

Related U.S. Application Data

(60) Continuation of application No. 13/783,143, filed on Mar. 1, 2013, now Pat. No. 8,805,514, which is a continuation of application No. 12/554,959, filed on Sep. 7, 2009, now Pat. No. 8,543,208, which is a division of application No. 10/060,045, filed on Jan. 29, 2002, now abandoned.

(51) Int. Cl.
| | |
|---|---|
| *A61B 5/00* | (2006.01) |
| *A61B 5/0482* | (2006.01) |
| *A61N 1/36* | (2006.01) |
| *A61N 1/372* | (2006.01) |

(52) U.S. Cl.
CPC .......... *A61B 5/0482* (2013.01); *A61N 1/36064* (2013.01); *A61N 1/36135* (2013.01); *A61N 1/37252* (2013.01); *A61N 1/37282* (2013.01); *A61N 1/37258* (2013.01)

(58) Field of Classification Search
CPC ...................... A61N 1/37235–1/37288; A61B 5/0002–5/0024
See application file for complete search history.

(56) References Cited

U.S. PATENT DOCUMENTS

| | | | |
|---|---|---|---|
| 5,029,590 A | 7/1991 | Allain et al. | |
| 5,292,343 A * | 3/1994 | Blanchette et al. | ............. 607/32 |

(Continued)

OTHER PUBLICATIONS http://www.medtronic.com/physician/activa "ACTIVA Therapy Overview" 1996.

(Continued)

*Primary Examiner* — Scott Getzow
(74) *Attorney, Agent, or Firm* — Arent Fox LLP

(57) ABSTRACT

An interactive implantable medical device system includes an implantable medical device and a network-enabled external device capable of bi-directional communication and interaction with the implantable medical device. The external device is programmed to interact with other similarly-enabled devices. The system facilitates improved patient care by eliminating unnecessary geographic limitations on implantable medical device interrogation and programming, and by allowing patients, physicians, and other users to access medical records, history, and information and to receive status and care-related alerts and messages anywhere there is access to a communications network.

17 Claims, 23 Drawing Sheets

(56) References Cited

U.S. PATENT DOCUMENTS

| | | | |
|---|---|---|---|
| 5,749,908 | A | 5/1998 | Snell |
| 6,016,449 | A | 1/2000 | Fischell et al. |
| 6,073,046 | A | 6/2000 | Patel et al. |
| 6,249,705 | B1 | 6/2001 | Snell |
| 6,580,948 | B2 | 6/2003 | Haupert et al. |
| 6,738,671 | B2 | 5/2004 | Christophersom et al. |
| 6,782,292 | B2 | 8/2004 | Whitehurst |
| 2001/0031997 | A1 | 10/2001 | Lee |
| 2003/0074033 | A1 | 4/2003 | Pless et al. |
| 2004/0077967 | A1 | 4/2004 | Jordan |

OTHER PUBLICATIONS http://www.siumed.edu/neuro/epilepsy/news/pressreleasesNNSpress.htnnl, "Cyberonics Inc_Receives FDA Approval Market NeuroCybernetic Prosthesis System for the Treatment of Epilepsy" Jul. 16, 1997.

Wagner, H.R., et al., Suppression of Cortical Epileptiform Activity by Generalized and Localized ECoG Electroencephalogr. Clin. Neurophysiol. 1975; 39(5): 499-506.

Sherman, D., "High-Tech Heart Devices Deliver Data Over the Web," Reuters News Service (Aug. 8, 2001).

Medsearch Technologies, Inc., "MedSearch Technologies, Inc. Develops a Revolutionary Home-Care Wireless Technology Utilizing PDAs—Personal Organizers—As Patient Monitors," Business Wire (Sep. 25, 2000).

Emerson, D., "Technology Puts Help on the Line," Minneapolis-St. Paul Business Journal (Dec. 17, 1999).

Quality of Life in Epilepsy Inventory: QOLIE-10, Patient Inventory Professional Postgraduate Services, a Division of World Communications Group (1993).

Vickrey, B. et al., "Quality of Life in Epilepsy QOLIE-31 (Version 1.0), Scoring Manual and Patient Inventory," Postgraduate Services, a Division of Physician's World Communications Group (1993).

Vickrey, B. et al., "Quality of Life in Epilepsy QOLIE-89 (Version 1.0), Scoring Manual and Patient Inventory," Postgraduate Services, a Division of Physician's World Communications Group (1993).

Cramer, J.A., et al., "A Brief Questionnaire to Screen for Quality of Life in Epilepsy: The QOLIE-10," Epilepsia 37(6): 577-582 (1996).

Cramer, J., et al., "Development and Cross-Cultural Translations of a 31-Item Quality of Life in Epilepsy Inventory," Epilepsia (1998) 39(1): 81-88 (1998).

Devinsky, Orrin, et al., "Development of Quality of Life in Epilepsy Inventory," Epilepsia (1995) 36(11): 1089-1104.

Vickrey, B., et al., "A Health-Related Quality of Life Instrument for Patients Evaluated for Epilepsy Surgery," Medical Care (Apr. 1992), vol. 30, No. 4, pp. 299-319.

Onuma, T., "Symposium II: Classification of Psychiatric Symptoms in Patients with Epilepsy," Epilepsia (2000) 41 (Suppl. 9): 43-48.

Lopez-Rodriguez, F., et al., "Personality Disorders Among Medically Refractory Epileptic Patients," J. Neuropsychiatry Clin. Neurosci. (Fall 1999) 11(4): 464-469.

Neppe, V. M., et al., "Modern Perspectives on Epilepsy in Relation to Psychiatry: Behavioral Disturbances of Epilepsy," Hospital and Community Psychiatry (Apr. 1988) 39(4): 389-396.

Neppe, V. M., et al., "The Application of the Screening Cerebral Assessment of Neppe (BROCAS SCAN) to a Neuropsychiatric Population," Journal of Neuropsychiatry (Winter 1992) 4: 85-94.

Dodrill, C.B., et al., "An Objective Method for the Assessment of Psychological and Social Problems Among Epileptics," Epilepsia (1980) 21: 123-135.

\* cited by examiner

SYSTEMS AND METHODS FOR INTERACTING WITH AN IMPLANTABLE MEDICAL DEVICE

CROSS-REFERENCE TO RELATED APPLICATION(S)

This application is a continuation of U.S. patent application Ser. No. 13/783,143, filed on Mar. 1, 2013, now U.S. Patent No. 8,805,514, which is a continuation of U.S. patent application Ser. No. 12/554,959, filed on Sep. 7, 2009, now U.S. Pat. No. 8,543,208, which is a divisional of U.S. patent application Ser. No. 10/060,045, filed Jan. 29, 2002, now abandoned, each of which are assigned to the owner of the present application and are incorporated by reference herein in their entirety.

BACKGROUND

1. Field

The invention relates to implantable medical device systems, and more particularly to implantable medical device systems having the ability to communicate with devices outside of a patient for programming, interrogation, data retrieval, and other purposes.

2. Background

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are generally electrographically defined as periods of abnormal neurological activity. As is traditional in the art, such periods shall be referred to herein as "ictal."

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp. ECoG signals, deep-brain counterparts to EEG signals, are detectable via electrodes implanted on or under the dura mater, and usually within the patient's brain. Unless the context clearly and expressly indicates otherwise, the term "EEG" shall be used generically herein to refer to both EEG and ECoG signals.

As is well known, it has been suggested that it is possible to treat and terminate seizures by applying electrical stimulation to the brain. See, e.g., U.S. Pat. No. 6,016,449 to Fischell et al., and H. R. Wagner, et al., "Suppression of cortical epileptiform activity by generalized and localized ECoG desynchronization," Electroencephalogr. Clin. Neurophysiol, 1975; 39(5): 499-506. And as stated above, it is believed to be beneficial to perform this stimulation only when a seizure (or other undesired neurological event) is occurring or about to occur, as inappropriate stimulation may result in the initiation of seizures.

It is especially beneficial to be able to tailor the operation of a neurostimulator (i.e., a device, preferably implantable, that delivers responsive electrical stimulation therapy as described above) to the specific needs of the patient. Accordingly, many neurostimulators and other implantable medical devices available and in development (in particular cardiac devices, such as pacemakers and implantable cardioverter-defibrillators, or ICDs) are programmable to some extent. Typically, however, programming and interrogation are performed with an expensive custom piece of equipment kept by the patient's hospital or clinic. To the extent a handheld or portable programmer is available to a patient, it is generally a standalone unit provided with a limited number of features and functions to avoid undesirable interference with the implantable device's clinical objectives.

With traditional solutions, device interrogation and programming can generally only be accomplished locally, i.e., in close proximity to the device being interrogated or programmed. Programmers and handheld control devices are relatively commonplace, but generally are not very sophisticated. Handheld devices are generally restricted to controlling a relatively small number of device parameters. Even other types of programmers typically are not sophisticated enough to be tied into multiple other devices or to have any ability to update or examine a patient's comprehensive treatment history, especially if the patient has not used that programmer before. Interaction with implantable medical devices has traditionally been limited by geographical considerations in the past.

It will be appreciated that it is desirable to have improved flexibility in managing patient care by enabling remote interrogation, programming, and interaction with implanted medical devices.

Modern implantable medical devices, such as neurostimulators, pacemakers, and ICDs, are capable of not only monitoring patient condition and delivering therapy, but also can store detailed data and diagnostics relating to a patient's condition for later retrieval. Analysis of this data can improve patient care dramatically, and allow fine-tuning the performance of the implantable devices by programming them with new operational parameters. Interrogation of an implantable medical device allows data stored in the device to be retrieved by an external device (which, presumably, is better equipped to analyze the data in great detail). After analysis, reprogramming the device allows its performance to be optimized based on the interrogated data.

In addition to the clinical utility provided by flexible interrogation and programming capabilities as described above, it is also desirable to be able to provide additional communications features to keep patients involved, informed, and invested in their own care. Traditional implantable medical devices, even those using programmers or hand-held control devices, are not well suited for this. Long-term care of epilepsy and cardiac patients, among others, requires a serious commitment from not only medical and clinical personnel, but also from patients. As described above, anti-epileptic drugs often have unpleasant side effects, so patients taking them should be made to feel like they have the information and control they need to effectively manage their disease, or they may become complacent and non-compliant. The same is true for patients with implantable medical devices—there is a danger that patients will take their devices for granted unless they are sufficiently involved.

Finally, it should be recognized that several tasks involved in the long-term care and management of neurological and cardiac patients are either labor-intensive or require inconvenient periodic office (or hospital) visits, even when the patient is being managed very well. It would be desirable to provide a mechanism for remote welfare-checks on patients with implantable devices, to allow their progress to be checked and data analyzed without the need for frequent office visits. Such a capability would preferably allow the user to store logs and notes regarding his or her condition, and would also facilitate the remote administration of examinations or surveys, as desired by the patient's treating medical team or physician.

Several others have attempted to leverage modern communications capabilities in the context of an implantable medical device system.

Medtronic, Inc. has tested an implantable diagnostic monitor for use in treating high-risk cardiac patients. See D. Sherman, "High-Tech Heart Devices Deliver Data Over the Web," Reuters News Service (Aug. 8, 2001). However, the Medtronic devices used in the "Chronicle Study" appear to be monitors only and do not appear to provide therapy. It would be preferable to have a device that is not only a continuous monitor, but is also a closed-loop treatment system that can be programmed and optimized with information obtained via the monitoring function.

Medtronic also has available a programmable implantable pulse generator for treating neurological disorders, particularly tremor. The "Activa" device has several programmable settings, but is not enabled for diagnostic data storage and upload, and generally provides only continuous (or semi-continuous) pulse streams, not closed-loop therapy responsive to the detection of a relevant event. It is not adapted for remote control or administration.

Another company has developed a PDA-based system for monitoring patient status. See "MedSearch Technologies, Inc. Develops a Revolutionary Home-Care Wireless Technology Using PDAs—Personal Organizers—as Patient Monitors," Business Wire (Sep. 25, 2000). However, the MedSearch system uses disposable sensors, and does not appear to tie into an implantable device system. Although a system such as the one from MedSearch might provide some additional convenience in the form of reduced office visits, it is not directly involved in a closed-loop treatment system and hence would not facilitate comprehensive remote patient care and management, only monitoring.

St. Jude Medical, Inc. developed the Housecall trans-telephonic data link system for implantable cardiac care devices. This device enabled the transmission of stored data and diagnostics from the implantable device to a remote location. However, the apparatus was relatively cumbersome, and it took a relatively long time to complete a single session of data transmission, leading to patient non-compliance. Like the systems described above, the Housecall system was intended to provide a remote monitoring function only, and did not serve as part of a closed-loop treatment system providing remote patient care.

Cyberonics, Inc. markets an implantable device for treating epilepsy; it is now also being tested for treating other disorders. The Cyberonics "NCP" (Neurocybemetic Prosthesis) is, in essence, an implantable pulse generator adapted, in this case, to apply electrical stimulation to the patient's vagus nerve. Like the Medtronic Activa, it applies a continuous or semi-continuous pulse stream, and only a few basic settings are programmable. It is not adapted to collect data or to provide responsive therapy, and no integrated system for network communications is available.

Clearly, an interactive implantable medical device system with enhanced network communications capabilities, geographic independence, and closed-loop treatment functionality would be desirable as it would greatly improve patient care and management for numerous diseases and disorders now treated with implantable devices that have only limited communications capabilities.

SUMMARY

An interactive implantable medical device system according to the invention avoids the shortcomings of the systems described above by enabling great flexibility and control over patient management and care in a closed-loop treatment system centering around the implantable device.

More specifically, an interactive implantable medical device system according to the invention generally includes, in addition to the implantable medical device, at least one external device capable of bi-direction communication and interaction with the implantable medical device. Preferably, the external device, which takes the form of a handheld computing device, a base unit used in the patient's home, or a physician-operated programmer, is also enabled to access a communications network and interact with other similarly-enabled devices, such as other programmers and a database.

The capabilities of an interactive implantable medical device system according to the invention facilitate improved patient care by eliminating unnecessary geographic limitations on device interrogation and programming—anywhere there is access to a communications network a patient's medical device can be queried and updated as necessary. A physician at a remote location can easily retrieve data not only from the implantable device but also from the patient's handheld computing device (which may include notes, annotations, seizure logs, and the results of any surveys or examinations requested by the physician or the system), analyze it in whatever manner is most convenient and effective, derive new device settings from the data, and program the device remotely to accept the new parameters. The kind of detailed analysis allowed by a system such as the one described herein, which allows the consideration of a far greater amount of diagnostic information than traditionally available, further facilitates a greater understanding of the patient's condition and, ideally, any imminent risks. This is especially true because the remote data collection and update capabilities allow data to be collected more frequently, allowing a patient's status and progress to be tracked in greater detail, even if the patient is not nearby. If a risk or some other urgent circumstance is observed, the system permits messages and alerts to be provided to the individuals who might need them—the patient, the patient's physician, and even field clinical support personnel if a device malfunction is suspected.

The system also permits a patient to have a much greater involvement and investment in his or her course of treatment, if such involvement is clinically desirable. Through the use of the handheld computing device, the patient can receive information, alerts, and messages about his or her condition, from the implanted device itself or from the communications network. If the patient has concerns about how the device is operating, a message can be sent to a physician or a note can be stored for later retrieval. This facilitates improved follow-up, even when the patient's physician is not easily reached.

BRIEF DESCRIPTION OF THE DRAWINGS

These and other objects, features, and advantages of the invention will become apparent from the detailed description below and the accompanying drawings, in which.

DETAILED DESCRIPTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
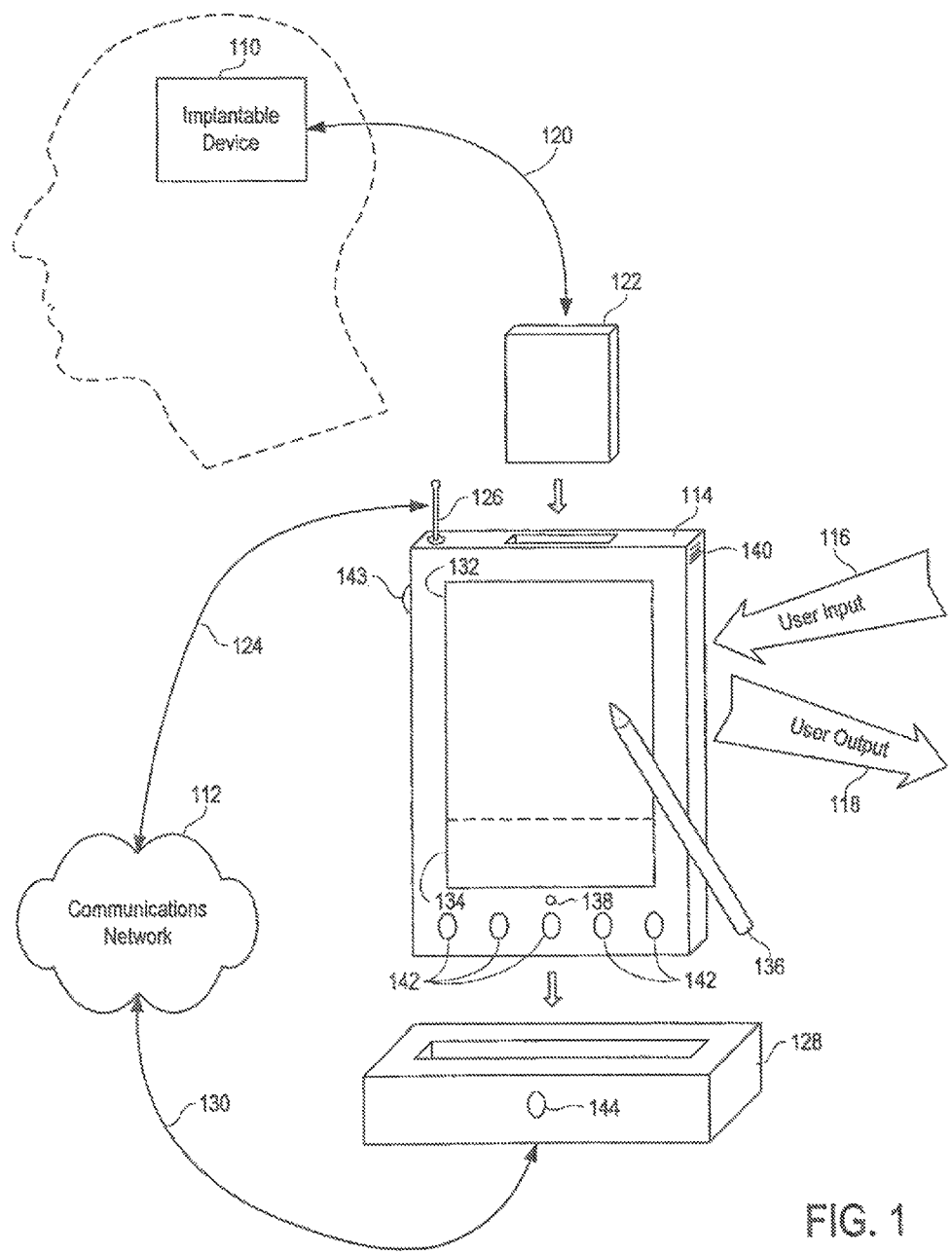
FIG. 1 is a diagram illustrating an exemplary basic exemplary personal control unit (PCU) for use with an implantable device and a communications network according to the invention.

Referring initially to FIG. 1, an implantable device 110 is illustrated. In the disclosed embodiment of the invention, the implantable device is a programmable neurostimulator for the treatment of epilepsy and other neurological disorders. See U.S. application Ser. No. 09/896,092, filed on Jun. 28, 2001, for a description of an exemplary neurostimulator; U.S. Pat. No. 6,016,449 to Fischell et al. contains illustrative details of an alternative embodiment.

The present invention enables communication between the implantable device 110 and a communications network 112 (such as the Internet) by way of a personal control unit (PCU) 114 or a similar device (various embodiments of which will be described in greater detail below). The PCU 114 is adapted to receive user input 116 and to pass it along to the communications network 112 or the implantable device 110, as appropriate, and also to receive information from the communications network 112 and the implantable device 110 and pass that information as user output 118. It should be noted that the term "PCU" is used herein for any apparatus of the sort used to interact with an implantable medical device system according to the invention, even if control is not specifically possible and the device is used only for monitoring purposes.

The PCU 114 communicates with the implantable device 110 via a wireless link 120 (typically inductive or RF), which in an embodiment of the invention is accomplished through a special-purpose expansion module 122 adapted to couple to an expansion connector of the PCU 114. In this embodiment, the PCU 114 need not include a substantial amount of custom hardware; it can be little more than a standard personal digital assistant (PDA), such as a Palm Pilot®, PocketPC®, or other portable (and preferably handheld) computing device, programmed and interfaced to accomplish the objectives described herein.

The PCU 114 typically also includes at least one data link 124 to the communications network 112. If the PCU 114 includes a built-in wireless communication capability (operating under any of several known protocols, such as IEEE 802.11b, Bluetooth, or digital cellular), an antenna 126 might be built into the PCU 114 to facilitate the data link 124. Alternative versions of the data link 124 are also possible, including part-time wired links (such as USB and Ethernet) from either the PCU 114 or a docking station 128 to the communications network 112. Even if a wireless version of the data link 124 is available, it may be desirable in some circumstances to also have a secondary link 130 from the docking station 128 to serve as a backup or alternative, operating only when the PCU 114 is docked in the docking station 128, in case the wireless data link 124 is either unavailable or undesired (e.g., in a hospital, airplane, or other electromagnetic interference-sensitive environment). Some of all of the data links described above can be accomplished either directly or through intermediate nodes and interfaces, such as remote access servers.

The PCU 114 is operated in a manner similar to PDAs and other PDA-like devices. Generally, a touch-sensitive screen is provided for user input and output 116 and 118. A touch-sensitive input portion 134 is reserved for writing with a stylus 136. In an alternative embodiment of the PCU 114, a keyboard might be provided. Audio input and output, uses of which will be described in further detail below, are accomplished with a microphone 138 and a speaker 140. For navigation and command purposes, several buttons 142 are provided on the PCU 114. These buttons can be used to command the PCU 114 to initiate special actions in a system according to the invention, or can have the usual function assigned to such buttons in a standard PDA. A docking station button 144 is also available to indicate when it is desired to "synchronize" (i.e., send and receive) data between the PCU 114 and the communications network 112.

While the PCU 114 illustrated in FIG. 1 greatly resembles a traditional PDA in form and operation, specialized peripherals and programming enable operation of the PCU 114 according to the invention. It should also be noted that alternative embodiments of the PCU 114 might take very different physical forms. For example, instead of a handheld PDA-like design, a relatively stationary home base unit with a display, input provisions (such as a keyboard), and interfaces might also be used. A personal computer with the necessary interface peripherals (along the lines of the expansion module 122 and the antenna 126) and software might also be used. These and other possible embodiments will be described in further detail below.

Figure 2:
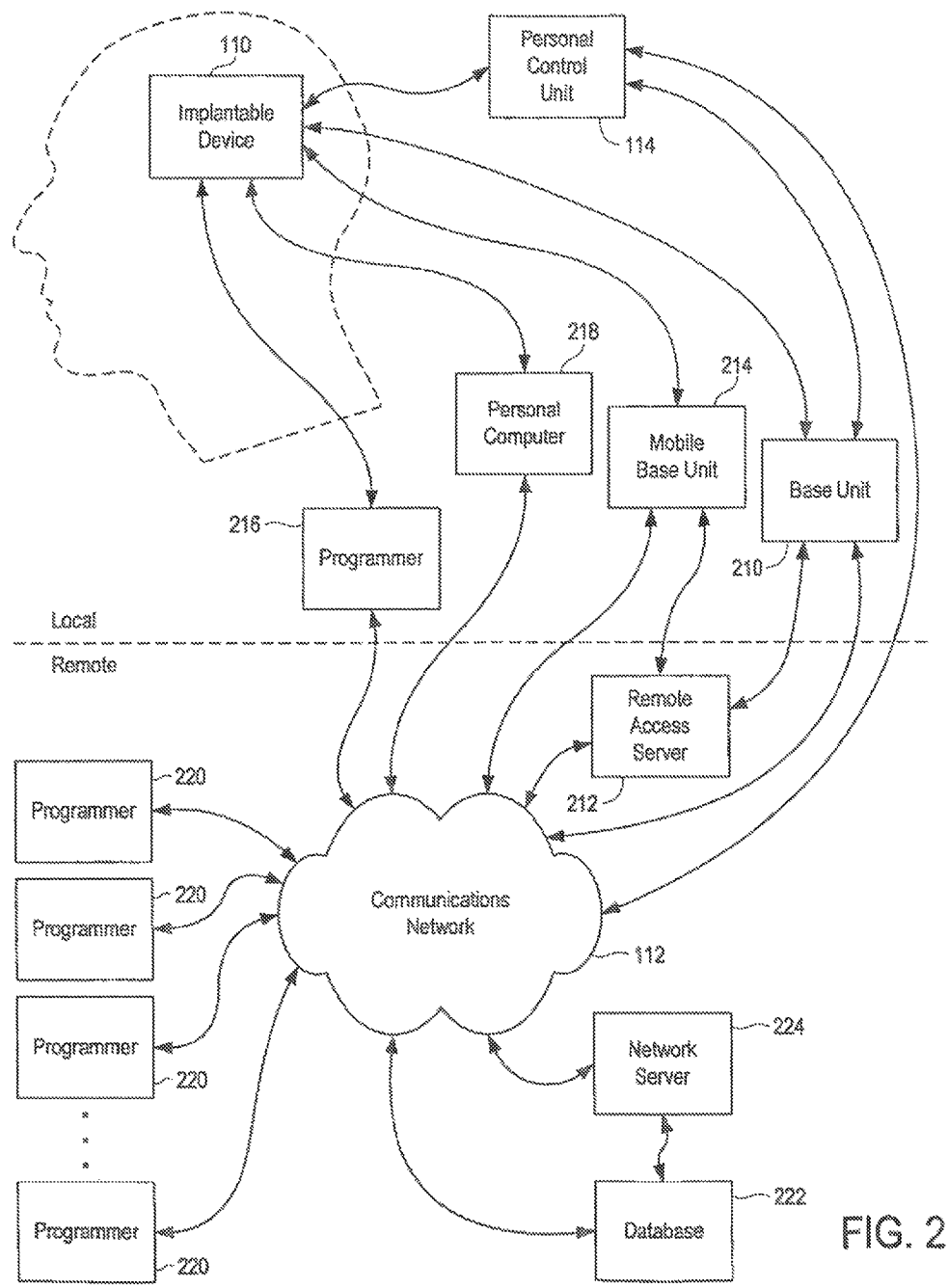
FIG. 2 is a block diagram illustrating an exemplary implantable device in communication with several illustrative network unit types according to the invention.

FIG. 2 illustrates an exemplary network configuration according to the invention. Accordingly, the network units illustrated in FIG. 2 are intended to depict a wide variety of different devices and configurations according to the invention, and likely do not reflect a real-world network topology or configuration.

The implantable device 110 is capable of communication with a wide variety of external devices. In addition to the PCU 114, the implantable device 110 is adapted for communication with a base unit 210 (which is in turn adapted for communication with the communications network 112 either directly or through a remote access server 212), a mobile base unit 214, a programmer 216, and a properly equipped personal computer 218.

As described above, the PCU 114 is generally a handheld computer with enhanced communications capabilities and special-purpose programming for use in a system according to the invention. The base unit 210 is similar, but typically is a larger device not intended for mobile use. Accordingly, because of the different physical configuration, some changes in equipment are possible and desirable. For example, a base unit according to the invention would typically include a data entry keyboard, a relatively larger display screen, and in most cases a wired network connection (analog modem, ISDN, telephone line DSL, or DOCSIS on coaxial cable), Ethernet, and other connectivity schemes are among the possibilities).

In an embodiment of the invention, since the base unit is not mobile or portable, a hand-held "wand" coupled to the base unit 210 is included to establish a short-distance communication link between the implantable device 110 and the base unit 210. A similar apparatus may be used with the programmer 216 or the personal computer 218 to enable communications with the implantable device. Details of an exemplary wand will be described in further detail below. It should be noted, however, that no separate wand may be necessary if a longer-distance (e.g., at least several meters) communications link is possible between the implantable device 110 and the base unit 210, or if the base unit 210 communicates with the implantable device 110 exclusively through the PCU 114.

The base unit 210 is suitable for use by patients (and caregivers) who either cannot or prefer not to carry the PCU 114. It can also be used in connection with the PCU 114, enabling a patient, caregiver, or other user to take advantage of the potentially larger form factor and other features (such as a full-sized keyboard and/or display screen) to more easily read and enter data and commands.

As referenced above, in one embodiment of the invention, the base unit 210 serves as an intermediary between the PCU 114 and the communications network 112. In this embodiment, the PCU 114 is provided with a relatively short-range network data link 124 (FIG. 1), such as one that uses the IEEE 802.11b wireless networking protocol. The range of such a network data link 124 should be sufficient for convenient use. Alternatively, to give one example, the docking station 128 for the PCU 114 can be connected via a wired link to the base unit 210, which would then complete the network data link 124 to the communications network 112 by periodically establishing a trans-telephonic connection to the remote access server 212.

The remote access server 212 is an apparatus that allows communications between any of the network units 114, 210, 214, 216, and 218 of the invention and the communications network 112. It is not necessary in all circumstances (for example, when one or more of the network units have a direct interface to the communications network), but frequently is employed to translate between the protocols used for short-range and point-to-point networking (typically used on the "local" side 226 of the system illustrated in FIG. 2—i.e., relatively near the patient with the implantable device 110) and the backbone technologies used by the carriers and providers that provide access to the communications network 112 (on the "remote" side 228 of the system—i.e., relatively far from the patient with the implantable device 110), for example via T1, T3, OC3, OC12, OC48, or OC192 lines. Accordingly, to accommodate geographically distributed users of a system according to the invention, multiple remote access servers would generally be used, and to accommodate different local and remote communications protocols, multiple different types of remote access servers (such as modem pools, wireless network base units, LAN-to-WAN bridges and routers, and other network interfaces and points of presence) can be employed. The single remote access server 212 illustrated in FIG. 2 is intended to be illustrative in nature, and as shown, allows the base unit 210 and the mobile base unit 214 to connect to the communications network 112. Other network configurations are of course possible and consistent with the invention described herein.

The programmer 216 is a device that is typically operated by medical personnel (such as the patient's treating physician) to control the operation of the implantable device 110. In general terms, the programmer 216 functions as a clinical interface to the implantable device 110, allowing its parameters to be modified, and for data and/or program code to be uploaded from and downloaded to the implantable device 110. For a more detailed explanation of an exemplary programmer, see U.S. patent application Ser. No. 09/977,052, filed on Oct. 12, 2001. Any given programmer may be located near the patient (as is the local programmer 216) or at a remote location (as are the remote programmers 220). Unless it is desired to directly interrogate or program the implantable device 110 using the local programmer 216, any of the programmers available in a system according to the invention can be used to perform various programming functions. This will be explained in further detail below.

A system according to the invention includes a database 222 and a network server 224. The database serves as a centralized data repository for all data relevant to the operation of the system, and may include clinical data, program code, and more. The centralized nature facilitates the use of remote programmers 220 and any other remote equipment enabled in a system according to the invention, as none of the programmers, base units, computers, or PCUs are necessarily 100% reliant on locally stored data. One or more of these devices is preferably configured to obtain data from and store data in the database 222. Accordingly, even if one of the remote programmers 220 has had no experience with a particular patient or implantable device 110, the database 222 is accessible to retrieve all of the information that would otherwise have been located only in the local programmer 216.

The network server 224 acts as the primary interface between the database 222 and other devices attached to the communications network 112. Although it might be possible and advantageous in certain circumstances to communicate directly with the database 222, it is generally preferable to configure the network server 224 to receive queries, perform necessary authentication, access the database 222, and respond as necessary, thereby reducing the processing load on the database 222 and also reducing the exposure of the database 222 to network traffic (thereby improving security).

It should be noted that although a single database 222 and a single network server 224 are depicted in FIG. 2, this configuration is only an exemplary functional depiction of network structure. It is possible to achieve the goals of the present invention with multiple databases and/or network servers, and it may be advantageous in certain circumstances to use a distributed data repository rather than a centralized one, to facilitate load balancing and to increase reliability in the event of network and equipment outages.

It will be recognized that the network configuration illustrated in FIG. 2 (like similar network configurations also within the scope of the invention) enables continuity of treatment during travel by patient, clinician, or both. The multiple remote programmers 220 (or even a single programmer attached to the communications network 112 remotely) allow a treating clinician or other authorized individual to monitor and treat patients, adapt or change settings on the implantable device 110, or administer various aspects of the system from afar. And in addition to the remote programmers 220 illustrated in FIG. 2, it is possible to have remote base units and PCUs, operated by the patient, a caregiver, or a clinician, capable of interaction with the system.

Figure 3:
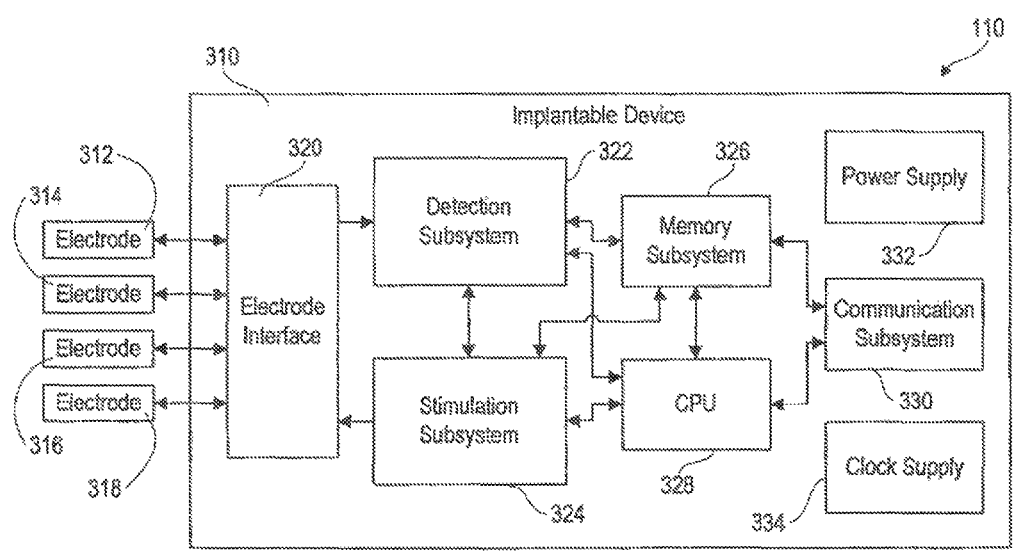
FIG. 3 is a block diagram of an embodiment of an implantable device according to the invention.

An overall block diagram of the implantable device 110 used for measurement, detection, and treatment according to the invention is illustrated in FIG. 3. Inside the housing of the device 110 are several subsystems making up a control module 310. The control module 310 is capable of being coupled to a plurality of electrodes 312, 314, 316, and 318 for sensing and stimulation. Although four electrodes are shown in FIG. 3, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise.

The electrodes 312-318 are connected to an electrode interface 320. Preferably, the electrode interface is capable of selecting each electrode as required for sensing and stimulation; accordingly the electrode interface is coupled to a detection subsystem 322 and a stimulation subsystem 324. The electrode interface also may provide any other features, capabilities, or aspects, including but not limited to amplification, isolation, and charge-balancing functions, that are required for a proper interface with neurological tissue and not provided by any other subsystem of the implantable device 110.

The detection subsystem 322 includes an EEG analyzer function. The EEG analyzer function is adapted to receive EEG signals from the electrodes 312-318, through the electrode interface 320, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., incorporated by reference above; additional inventive methods are described in detail below. The detection subsystem may optionally also contain further sensing and detection capabilities, including but not limited to parameters derived from other physiological conditions (such as electrophysiological parameters, temperature, blood pressure, etc.).

The stimulation subsystem 324 is capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 322. As illustrated in FIG. 3, the stimulation subsystem 324 and the EEG analyzer function of the detection subsystem 322 are in communication; this facilitates the ability of stimulation subsystem 324 to provide responsive stimulation as well as an ability of the detection subsystem 322 to blank the amplifiers while stimulation is being performed to minimize stimulation artifacts. It is contemplated that the parameters of the stimulation signal (e.g., frequency, duration, waveform) provided by the stimulation subsystem 324 would be specified by other subsystems in the control module 310, as will be described in further detail below.

Also in the control module 310 is a memory subsystem 326 and a central processing unit (CPU) 328, which can take the form of a microcontroller. The memory subsystem is coupled to the detection subsystem 322 (e.g., for receiving and storing data representative of sensed EEG signals and evoked responses), the stimulation subsystem 324 (e.g., for providing stimulation waveform parameters to the stimulation subsystem), and the CPU 328, which can control the operation of the memory subsystem 326. In addition to the memory subsystem 326, the CPU 328 is also connected to the detection subsystem 322 and the stimulation subsystem 324 for direct control of those subsystems.

Also provided in the control module 310, and coupled to the memory subsystem 326 and the CPU 328, is a communication subsystem 330. The communication subsystem 330 enables communication between the implantable device 110 (FIG. 1) and the outside world, particularly an external PCU 114 (FIG. 1), programmer 216 (FIG. 2), or other apparatus according to the invention. As set forth above, the disclosed embodiment of the communication subsystem 330 includes a telemetry coil (which may be situated outside of the housing) enabling transmission and reception of signals, to or from an external apparatus, via inductive coupling. Alternative embodiments of the communication subsystem 330 could use an antenna for an RF link or an audio transducer for an audio link.

Rounding out the subsystems in the control module 310 are a power supply 332 and a clock supply 334. The power supply 332 supplies the voltages and currents necessary for each of the other subsystems. The clock supply 334 supplies substantially all of the other subsystems with any clock and timing signals necessary for their operation.

It should be observed that while the memory subsystem 326 is illustrated in FIG. 3 as a separate functional subsystem, the other subsystems may also require various amounts of memory to perform the functions described above and others.

Furthermore, while the control module 310 is preferably a single physical unit contained within a single physical enclosure, namely the housing, it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 328 and the other functional subsystems may also vary—the functional distinctions illustrated in FIG. 3 may not reflect the integration of functions in a real-world system or method according to the invention.

Figure 4:
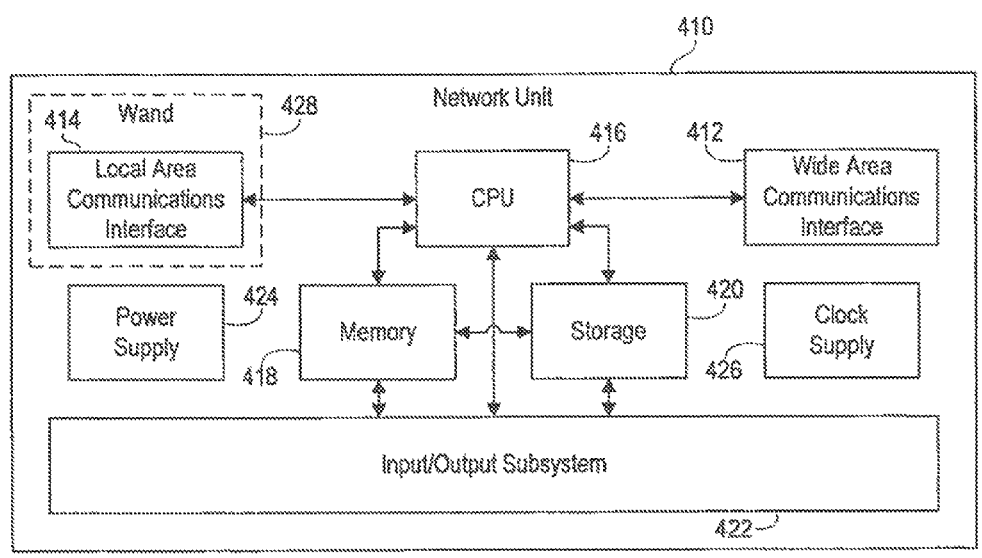
FIG. 4 is a block diagram of an embodiment of a generic network unit according to the invention.

Referring now to FIG. 4, a block diagram representing a generic network unit 410 (of which the PCU 114, base unit 210, mobile base unit 214, programmer 216, and personal computer 218 of FIGS. 1-2 are all species) is set forth in detail.

The network unit 410 is a general-purpose or special-purpose computer programmed or adapted for use according to the invention. Accordingly, it includes a wide area communications interface 412 for communications with the communications network 112 (FIG. 1), and if it will be used to connect to other nearby devices (such as the implantable device 110, the PCU 114, or the base unit 210), it also includes a local area communications interface 414. Preferably, both the wide area communications interface 412 and the local area communications interface 414 are capable of bi-directional communications.

The network unit is controlled by a CPU 416. The CPU is coupled (either directly or through a bus controller, as is typical in the art of computer design) to the wide area communications interface 412, the local area communications interface 414, a memory subsystem 418 (which might include ROM, DRAM, and other random-access memory) for programming and short-term storage, a storage subsystem 420 (which might include a hard drive, flash memory, and other non-volatile storage), and an input/output subsystem 422 used to pass information to and receive information from a user. The input/output subsystem 422 will be described in further detail below with reference to FIG. 5.

The operation of the network unit is controlled by a power supply 424 and a clock supply 426. The power supply 424, in the case of a handheld unit such as the PCU 114, typically includes batteries, while other types of network units might receive power from AC outlets. A combination of the two sources (as is common with laptop computers) might also be used. The clock supply 426 supplies substantially all of the other subsystems of the network unit with any clock and timing signals necessary for their operation.

As with the implantable device 110, described above, it should be observed that while the memory subsystem 418 is illustrated in FIG. 4 as a separate functional subsystem, the other subsystems may also require various amounts of memory to perform the functions described herein and others. Furthermore, while the network unit 410 (excluding the wand 428, if any) is preferably a single physical unit contained within a single physical enclosure, namely the housing, it may comprise a plurality of spatially separate units each performing a subset of the capabilities described herein. Some of the functions or subsystems of the network unit 410 might be resident in a removable module, such as the expansion module 122 (FIG. 1). In particular, if a standard commercially available computing device is used for the network unit 410 (such as a laptop or desktop computer for the base unit 210 or the programmer 216), then certain features (such as the local area communications interface 414, to give one example) might be added via insertion of a commercial or custom peripheral, e.g., a PC Card. If a commercial handheld computer is used for the PCU 114, then other possibilities will be evident (e.g., a Springboard® module for the Handspring Visor® line of PDAs).

It should be noted that the various functions and capabilities of the subsystems of the network unit 410 described above may be performed by electronic hardware, computer software (or firmware), or a combination thereof. The illustration of FIG. 4 illustrates several of the major functional subsystems present in a network unit consistent with the invention. However, it should be noted that in many computing systems, other functional subsystems and modules are present that are not necessarily reflected in FIG. 4. Moreover, an actual network unit 410 according to the invention might integrate two or more of the above-referenced subsystems. For example, the wide area communications interface 412 and the local area communications interface 414 might be adapted into a single subsystem if efficiencies result therefrom. Accordingly, FIG. 4 is for purposes of illustration only, and does not necessarily reflect the actual configuration of the PCU 114, the base unit 210, the mobile base unit 214, the programmer 216, or the personal computer 218. It is, however, considered to be representative.

As described above, certain network units (such as the base unit 210, the programmer 216, or the personal computer 218) might include a connected but separate wand 428 to enable a short-range, e.g., inductive, wireless link to the implantable device. In such a network unit 410, the local area communications interface 414 is generally separate from the remainder of the network unit 410 and is coupled thereto via a wire or other connection.

Figure 5:
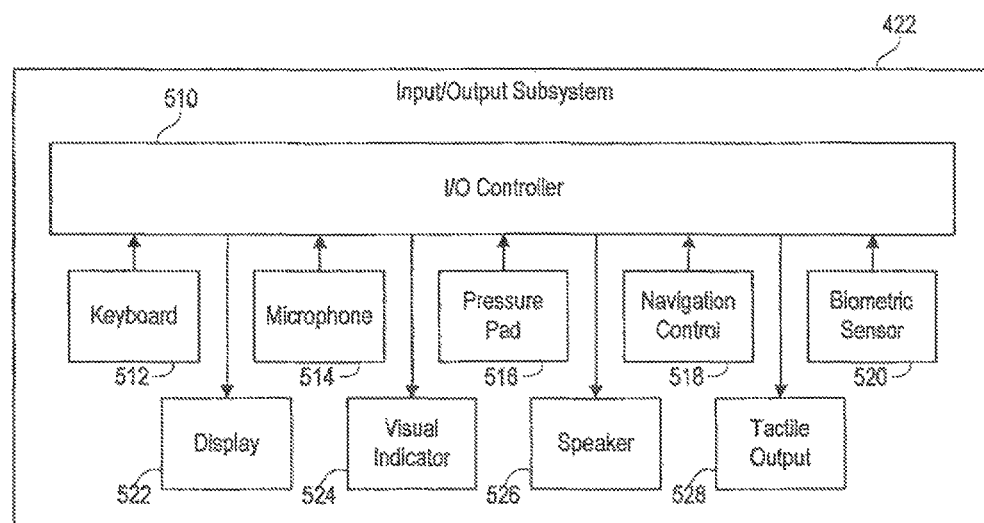
FIG. 5 is a block diagram of an exemplary I/O subsystem of the network unit illustrated in FIG. 4.

An exemplary embodiment of the Input/Output Subsystem 422 of FIG. 4 is illustrated in greater detail in FIG. 5. As shown, the Input/Output Subsystem 422 includes an I/O Controller 510 capable of coordinating the actions of various portions of the subsystem. One or more of the portions 512-528 of the Input/Output Subsystem 422 illustrated in FIG. 5 are optional; it should be noted that various embodiments of a network unit 410 according to the invention will generally include only a subset of the capabilities described herein. It would be unusual (though possible) for a network unit to include all illustrated input and output facilities.

Some input possibilities are as follows. A keyboard 512, such as a traditional computer keyboard, can be used in connection with larger network units (such as base units and programmers). On smaller units, a smaller keyboard 512 can be made available (such as that provided on the Blackberry® handheld device by Research In Motion), or a "soft keyboard" can be provided in conjunction with a touch screen, such as on the Palms handheld devices. It will be recognized that other data input paradigms are also possible (that may be considered analogous to a keyboard, in that alphanumeric and other data can be entered thereby) and known in the art; such alternatives might take the place of the keyboard 512 in a system according to the invention.

A microphone 514 (such as the microphone 138) can be used to receive audio input. This might be useful for several purposes, including recording audio messages for storage or transmission to remote locations, for data input via speech recognition, or for biometric authentication via voice recognition. Audio processing is relatively storage and computationally intensive, so a network unit 410 having speech recognition or voice recognition capabilities according to the invention would generally require a more powerful CPU 416 and more memory 418 and storage 420 than otherwise.

A pressure pad 516 (such as the input portion 134) can be used to receive tactile and gestural input in a system according to the invention. The pressure pad 516 can be used for data entry, for example handwriting recognition (either conventional handwriting or a special-purpose symbol set adapted for improved recognition accuracy, such as the Graffiti scheme used in Palm® handhelds). It can also be used as a pointing and selection device analogous to a "mouse" on a desktop computer system of the pressure pad found on many laptop computers. Other gestural sensors in addition to the pressure pad 516 are also possible; for example, position and orientation detectors might be used advantageously in a system according to the invention for data entry or pointing and selection.

A navigation control 518 (such as one or more of the buttons 142 or the jog wheel 143 of FIG. 1) is usable to effect pointing, selection, and navigation through numerous menus provided by the software of the network unit 410. In an embodiment of the PCU 114, for example, one or more of the buttons 142 might be adapted to interpret pushes in different directions as different navigational controls. Similarly the jog wheel 143 might be used to navigate upward or downward within a menu displayed on the PCU 114. In a desktop system, a mouse or trackball might be used instead of buttons or a jog wheel. Various other navigation controls are, of course, possible and consistent with the invention described herein.

A biometric sensor 520 is available in an embodiment of the invention to authenticate the user of the network unit 410. Exemplary biometric sensors include thumbprint, face, and retina scanners, keystroke timing recognition devices, and chemical signature detectors. Numerous other approaches are possible. Although the biometric sensor 520 might be provided in a network unit according to the invention, actual processing and authentication of biometric input need not be performed at the network unit 410 receiving the input. Instead, data representative of the biometric input would be sent to a remote location, such as the database 222, and processed there.

On a typical network unit 410, a display 522 is furnished to provide information to the user. On a handheld device, a liquid crystal display (LCD) is typically used, as the power and space requirements are relatively small. On larger systems, such as the base unit 210, a cathode ray tube (CRT) or other display mechanism might be feasible, although LCD technology is well suited for this application as well.

Aside from the display 522, a visual indicator 524 might also be provided. It is common for commercially available handheld devices to have one or more light-emitting diode (LED) visual indicators separate from the display, providing instant information regarding alerts and alarms, operational status, power supply, whether messages are waiting, and the like. It is contemplated that the visual indicator 524 in a system according to the information would similarly provide readily understood alert and status information.

A speaker 526 or other audio output device is furnished to provide for the possibility of alarms, data output (via, e.g., tones, tone sequences, music, arbitrary sounds, or even recorded or simulated speech). The speaker 526 can also be used to accomplish a data link via acoustic modulation (as in a traditional analog modem used for trans-telephonic data communications). It is envisioned that in a system according to the invention, the speaker 526 would generally be used to provide alerts and alarms to the user, though other uses are certainly possible and might prove advantageous in certain circumstances.

Finally, in the illustrative input/output subsystem illustrated in FIG. 5, a tactile output 528 is provided. The tactile output 528 might provide one or more of several possible tactile experiences to the user—a "nudge" sensation, a simulated texture, or (most probably) vibration to name but a few examples. The tactile output 528 can be used to provide information to the user, and a vocabulary of tactile sensations might be established to facilitate relatively complex outputs, but it is presently envisioned that a simple vibration alarm (as is often found on mobile telephones) is the most probable embodiment of the tactile output 528.

Consistent with the invention described herein (and with the illustration of FIG. 1), an embodiment of the PCU 114 would typically include a small LCD display, a pressure pad for navigation and data entry, buttons and controls for navigation control, a visual indicator for power and/or message status, and a speaker or other small audio transducer. Various embodiments of the PCU 114 might include a vibrating alert. The base unit 210, the programmer 216, or the personal computer 218 might include a relatively larger CRT or LCD display, a substantially full-sized keyboard, a microphone, a mouse or other pointing device for a navigation control, and sound reproduction capability. Likewise, the mobile base unit 214, though likely similar, might include a smaller display and keyboard. These configurations are intended for illustration only, and it should be noted that any aspect of the present invention might be alternatively configured if a different particular arrangement of capabilities is advantageous in any given context.

Figure 6:
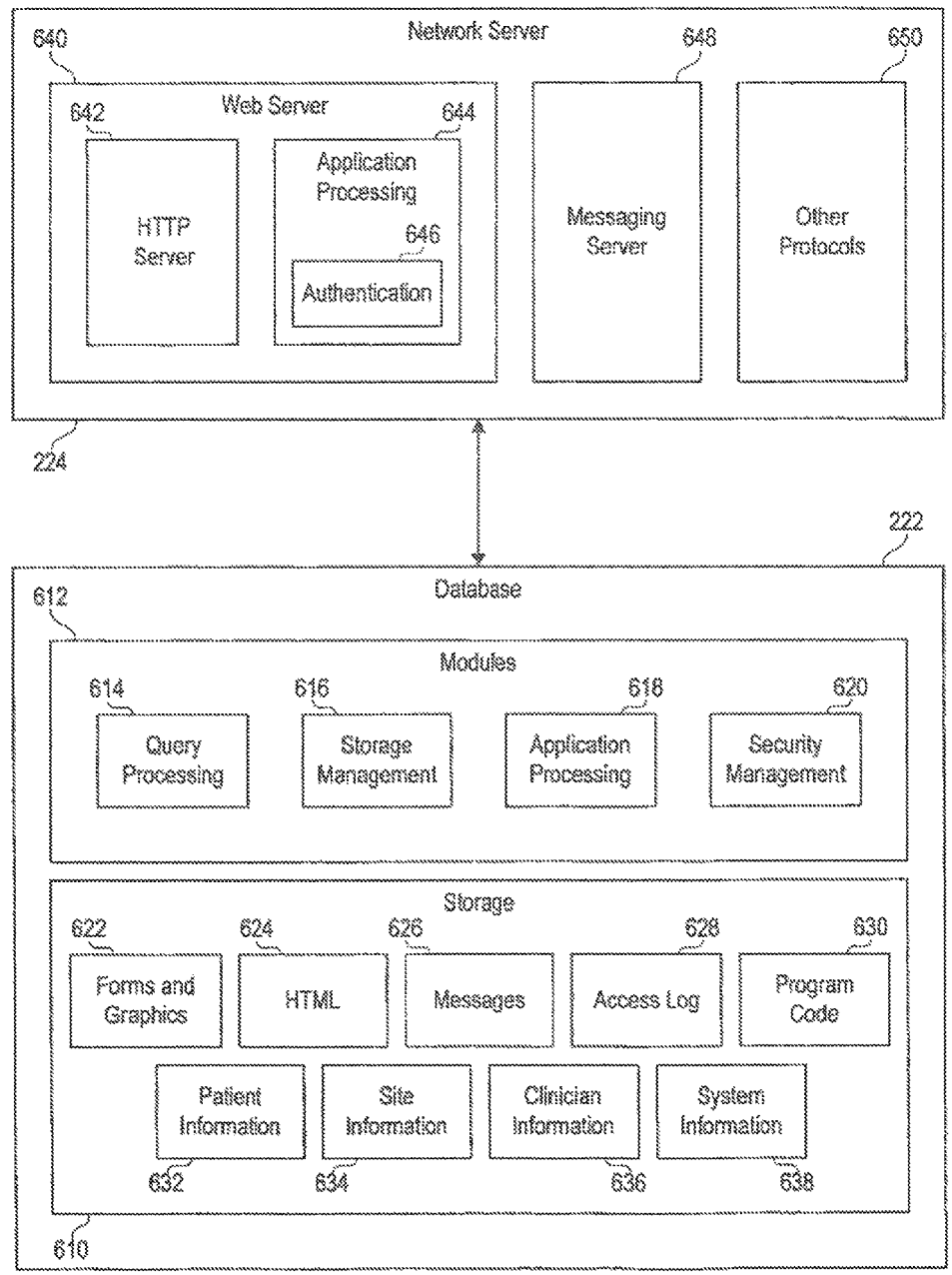
FIG. 6 is a block diagram of the functional structure of an exemplary database according to the invention.

FIG. 6 is an exemplary block diagram of the database 222 and its network server 224 employed in an implantable device system according to the invention. The database 222 and the network server 224 (which acts as an interface to the database 222) jointly serve as a widely accessible storage repository 610 for various data types, including program code, patient information, and other data, as will be described in detail below.

As illustrated, the database 222 performs query processing, storage management, application processing, and security management functions. These functions are performed by modules 612, including a query processing module 614, a storage management module 616, an application processing module 618, and a security management module 620, respectively. Each of the foregoing modules 614-620 is generally implemented as software on a database server computing system (represented herein by the database 610), although it should be noted that various modules may be combined in an implementation and that other modules might also be present. Furthermore, the modules described herein can be implemented in hardware, software, or a combination thereof.

The query processing module 614 is enabled to receive a query message from the communications network 112 (and hence any network unit 410 in a system according to the invention), process the query message and identify responsive data in the database 222, and respond to the originating device. Accordingly, the query processing module 614 performs a task that is fairly standard and common in database systems, though it should be noted that it is performed in a manner consistent with the invention described herein.

The storage management module 616 is programmed to track the various items of data stored in the storage 610 of the database 222, manage the allocation of space, perform backups, and the like. The functions performed by the storage management module 616 are also generally consistent with those performed by known databases, though there may be some differences suggested in the practice of the invention.

The application processing module 618 is adapted to execute computer programs (such as "servlets") intended for use at the database 222. For example, any data processing required to accomplish authentication (of users and devices), encryption, compression, and data management is generally performed by the application processing module 618 illustrated in FIG. 6.

The security management module 620 handles any data involved in user and device authorization and authentication, password management, and account management. Although the functions performed by the security management module 620 are similar in some ways to the functions performed by the query processing module and other capabilities of the database 222, the security functions are separated from other functions to increase reliability and resistance to attack.

It will be appreciated, as is indicated above, that the database 222 stores several types of information in its storage 610. In particular, the storage 610 includes two general categories of data: system data and operating data. The first category, system data (essentially the static content of the database 222, providing context for its operation), includes forms and graphics 622 used in collecting data from and reporting to the network units present in a system according to the invention; any HyperText Markup Language (HTML) code 624 and the like used to generate Web pages to be served to the system; a catalog of messages 626 in text, visual, audio, or other formats to be delivered to users of devices in the system (which can be provided in multiple languages for users who need non-English access); an access log 628 providing a detailed accounting of accesses (and attempted accesses) to the database 222 for audit purposes; and the operative program code 630 used by the database 222 (and particularly the application processing module 618). The second category, operating data (essentially the dynamic content of the database 222), includes patient information 632 (vital data of the patients enrolled in the system who have the implantable device 110), site information 634 (the facilities, such as hospitals, clinics, and assisted living homes, that are authorized and enabled to participate in the system), clinician information 636 (vital data of the physicians, nurses, and other personnel responsible for clinical patient management), and system information 638 (e.g., current information on the state of the devices in the system, authorization lists, password lists, storage and security policies, and other low-level information generally invisible and inaccessible to users).

Several exemplary relationships among the modules 612 and the various types of data in the storage 610 are set forth below.

The query processing module 614 uses the forms and graphics 622 to present a meaningful query context to a user, receives a query and stores it in the access log 628, and responds to the query using additional forms and graphics 622, the HTML 624, messages 626, program code 630, and any patient, site, clinician, or patient information 632-638 identified in processing the query. The query processing module 614 provides the response to the originating device, which may be the PCU 114, the base unit 210, the mobile base unit 214, the programmer 216 (or a remote programmer 220), the personal computer 218, or any other authorized network unit 410.

The storage management module 616 manages the dynamic content of the storage 610, particularly the patient, site, clinician, and system information 632-638.

The application processing module 618 is generally responsive to the program code 630. However, it should be recognized that the program code 630 may be written to require access to various other data in the storage 610, such as the patient, site, clinician, or system information 632-638.

The security management module 620 is operative to access the access log 628, the patient, site, and clinician information 632-636, and the system information 638 involved in data and system security (such as user names and passwords). If data processing is necessary in performing authorization or authentication checks, the program code 630 (and hence the application processing module 618) might also become involved in certain circumstances.

Other function-data relationships should be evident, and may vary according to the specific application. Additional details of the role of the database 222 in connection with the operation of the present invention will be further described below.

As generally described above, the database 222 communicates with the communications network 112 (FIG. 2) through the network server 224. Generally, accesses to the database 222 will occur through a web server 640 (one example of which is the Apache open-source web server) resident on the network server 224. The web server 640 includes an HTTP server 642 in communication with the storage 610 of the database 222. The HTTP server 642 processes and responds to any HTTP requests received by the web server 640. If any server-level programs are required to be run, an application processing capability 644 resident on the web server 640 is available to handle such needs. For example, tasks related to authentication 646 may be necessary before passing a request on to the security management module 620 of the database 222; the application processing capability 644 is operative to perform such tasks.

Although it is generally understood that most accesses to the database 222 will occur as HTTP requests arriving through the web server 640, it should be recognized that other access techniques are possible. For example, instant-messaging protocols might also be used to pass data to and from the database 222. A messaging server 648 is also resident on the network server 224; it is programmed to handle instant-messaging-type transactions. Other protocols are also possible, and a server program adapted to handle other protocols 650 might also be necessary or advantageous.

Figure 7:
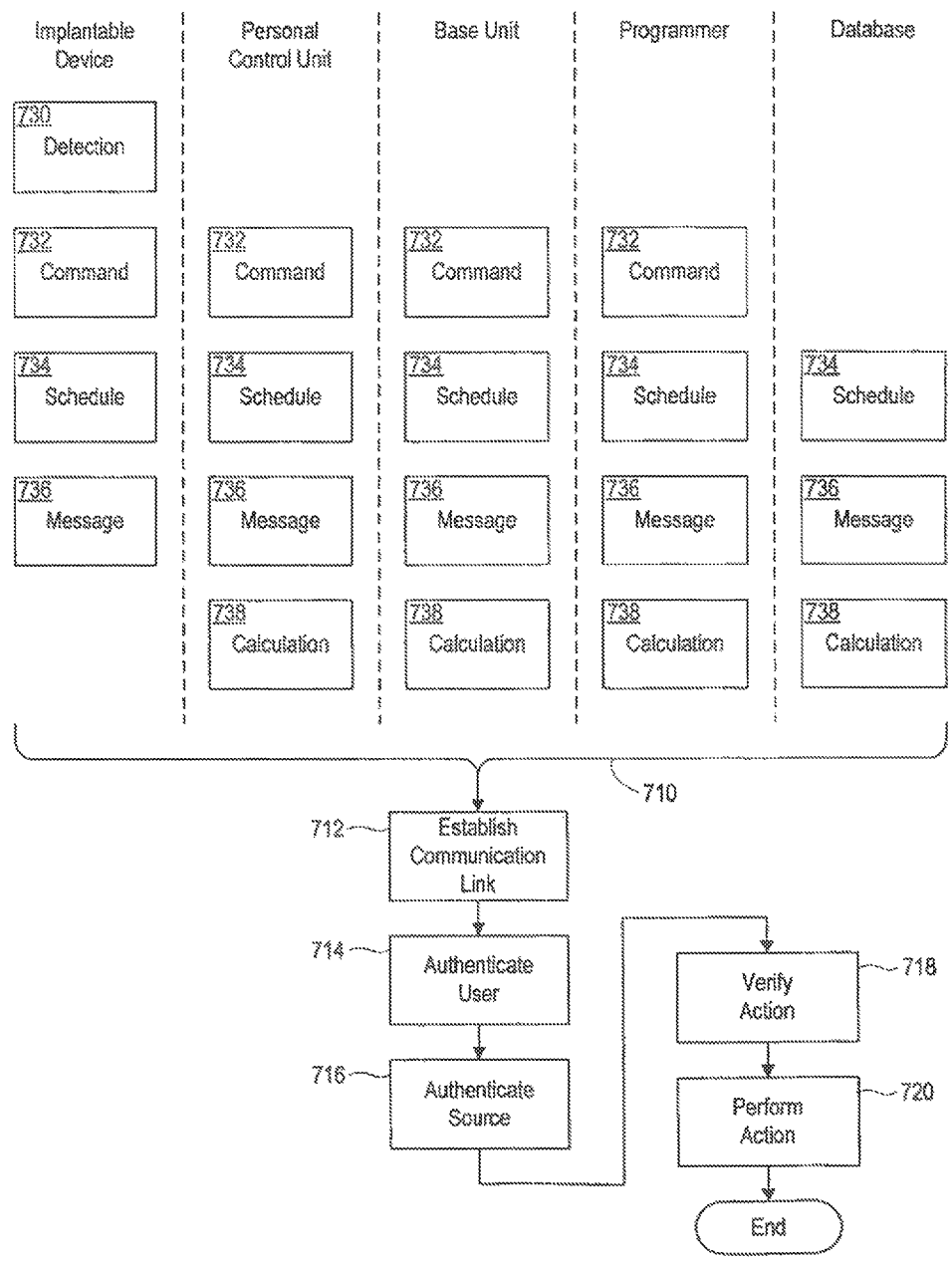
FIG. 7 is a flow chart illustrating an overall function and command chart with command sources and validation steps required to process commands.

FIG. 7 illustrates a number of possibilities representing procedures for initiating an action in an interactive system according to the invention.

A system according to the invention begins to perform an action upon receipt of one or more of a large number of possible initiating events 710. Although an action can be initiated at and performed by the same device in the system, that is not always or necessarily the case. Accordingly, it is instructive to consider the system in terms of an initiating device, where the chain of events leading to performance of an action begins, and an acting device, where the action is ultimately carried out. One or more additional network units may also participate in the process as supporting devices, acting as intermediaries, data sources, or simply as parts of the communications network 112.

In general, when an action is to be performed, a communication link is established (step 712) among the initiating device, the acting device and any supporting devices. To give one simple example, a physician at a remote location might command the interactive system to administer a quality of life survey to a patient. The process performed in doing so, and some details of quality of life surveys in general, will be described in greater detail below. In this case, one of the remote programmers 220, used by the physician, is the initiating device. The patient's PCU 114, used to administer the survey, is the acting device. There are several supporting devices: any intermediate communications nodes, such as the base unit 210 (between the communications network 112 and the PCU 114) used to relay information between the remote programmer 220 and the PCU 114; the database 222, where survey results are ultimately stored; and the network server 224, which is generally interposed between the communications network 112 and the database 222.

It should be noted that the communication link established in step 712 need not be real-time in all cases. To enable a system according to the invention when one or more network units are either disabled or disconnected from the network, certain data messages between network units can be deferred or queued by the transmitting device. Where a message has high urgency or importance, the deferral or queuing may be accompanied by a message to the user to establish a link (e.g., by docking the PCU 114, moving into range of the base unit 210, or connecting to a telephone line).

Figure 22:
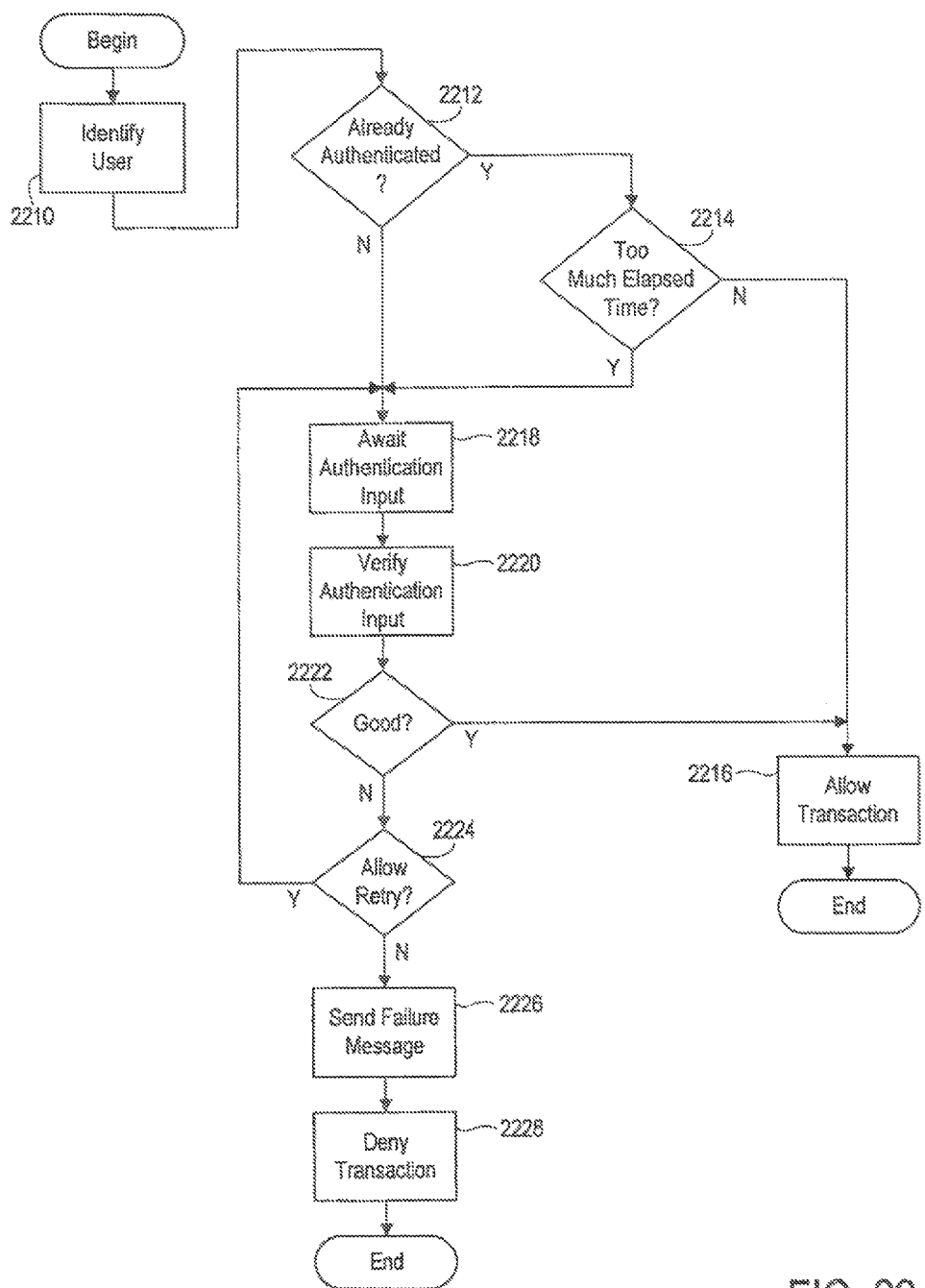
FIG. 22 is a flow chart illustrating an exemplary user authentication functional process performed according to the invention.

The user of the initiating device is then authenticated (step 714). Preferably, this is performed according to the method described below and illustrated in FIG. 22. In general terms, user authentication involves confirming with an authentication server, either locally or remotely, that the individual using the initiating device is who he or she claims she is. This can be accomplished through login names and passwords, biometrics, or any of a number of other known techniques.

The source, the initiating device itself, is then also optionally authenticated (step 716). This operation can be performed in a manner similar to the user authentication method set forth above. This is done to ensure that the interactive system of the invention is not being accessed by an unauthorized device, which might lead to problems (especially if the access attempts are malicious). The type of authentication data used to authenticate the source would generally be a numeric code or other unique identifier either preset or programmed into each network unit used in accordance with the system.

Like other transactions in a system according to the invention, user or source authentication can be deferred or queued if communication is not immediately possible. In this case, a system according to the invention would preferably conditionally allow the desired transaction (or at least any data entry related to the transaction), but not store it in the database 222 or elsewhere until authentication is successfully completed. In other cases, for example when potentially confidential patient records are requested, transactions may be disallowed if authentication cannot be completed in real time.

The nature of the action to be performed is then analyzed and verified against one or more allowability rules (step 718). The timeliness of the action (i.e., whether the action is being performed at an appropriate time, given the user's history) is considered according to the method described below and illustrated in FIG. 23, and if the user is attempting to perform certain actions too often or at improper times, the action may be denied. Other desired criteria might also be applied. For example, certain users might be locked out from certain functions.

Figure 19:
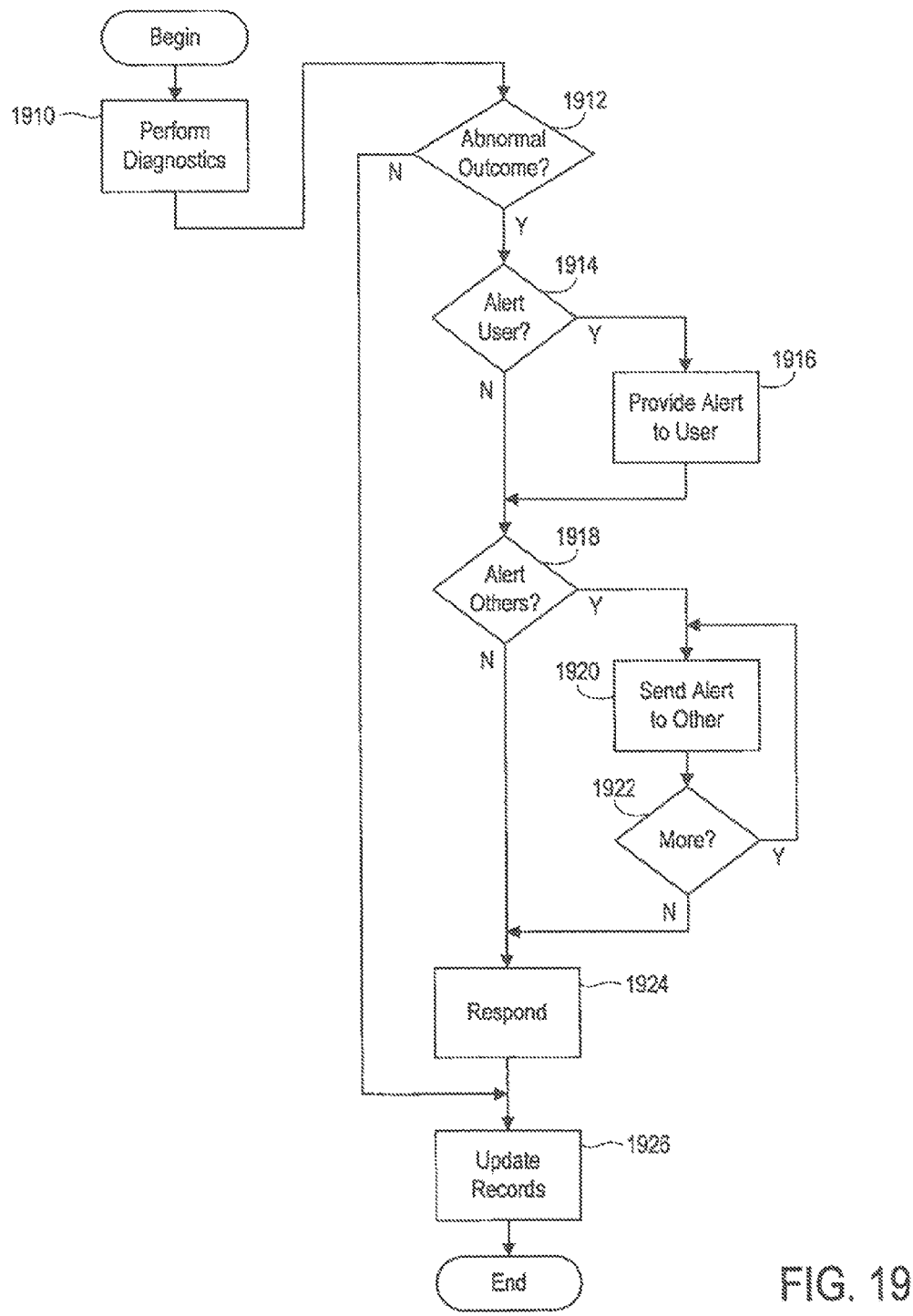
FIG. 19 is a flow chart illustrating an exemplary system diagnostics functional process performed according to the invention.
Figure 20:
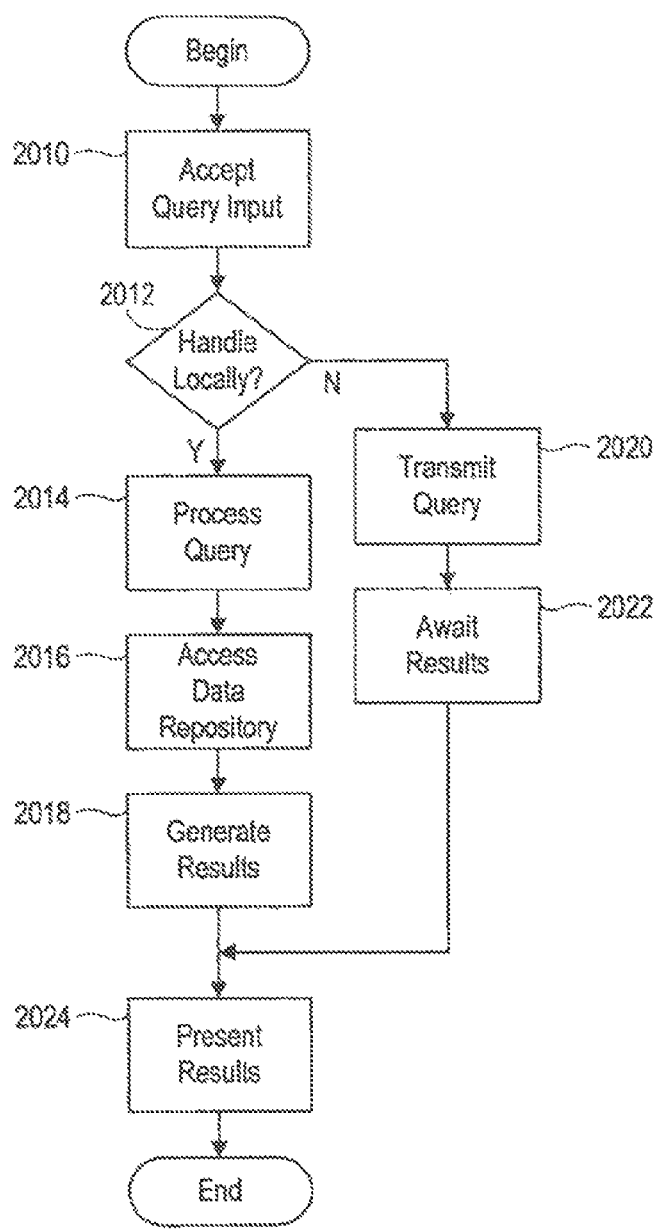
FIG. 20 is a flow chart illustrating an exemplary database query functional process performed according to the invention.

If user authentication, source authentication, and action verification all complete successfully, then the desired action is performed (step 720). As will be described in detail below, there are numerous possibilities for the action to be performed. In particular, it is possible to upload data from the implantable device 110 or any other network unit (see FIG. 8), to download software to the implantable device 110 or another network unit (FIG. 9), to download detection parameter sets to the implantable device 110 (FIG. 10), to handle the entry and storage of seizure logs (FIG. 11), to handle the administration and storage of quality of life surveys, neurophysiological exams, and the like (FIG. 12), to allow a command to be entered and processed (FIG. 13), to alert a device user to an urgent condition (FIG. 14), to enter a note or annotation pertaining to data (FIG. 15), to send a message (FIG. 16), to receive a message (FIG. 17), to monitor EEG or other data in real time (FIG. 18), to perform system diagnostics (FIG. 19), or to query a database (FIG. 20). Other actions are also possible and will be apparent to a practitioner of skill in the art.

As set forth above, a number of possible initiating events 710 can be used to cause one or more of the above-referenced actions to be performed. For example, a neurological event detection 730 (typically observed by the implantable device 110 of FIG. 1) can be used to initiate the transmission of a message to a physician, alert one or more device users (such as the patient), or both. A detection by the implantable device 110 or the PCU 114 that EEG storage is full or nearly full might also cause an alert and/or a message requesting that a data upload be performed.

Similarly, a command 732 entered at the implantable device 110 (e.g., by audio command, tapping, or magnet use), the PCU 114 (e.g., via any of its input capabilities), the base unit 210, or the programmer 216, can initiate nearly any of the possible actions performable by a system according to the invention. It is anticipated that each of the foregoing devices might be able to accept different types of commands. For example, the implantable device 110 might receive commands by moving a magnet into and away from the vicinity of the device; the PCU 114 might receive commands via button presses, handwriting recognition, or voice recognition; and the base unit 210, mobile base unit 214, programmer 216, and personal computer 218 might all receive commands from a keyboard or pointing device.

For example, pressing a button on the PCU 114 (or entering a command into the handwriting input portion 134) might initiate a data upload, a software download, a seizure log entry, a note entry, a message transmission, real-time EEG monitoring, or a database query, to name but a few likely actions. Pressing a GUI button on the programmer 216 might initiate a data upload, a parameter download, real-time monitoring, or numerous other options. There are too many possibilities to list them all; they would be apparent to a practitioner of ordinary skill in the art.

Various actions might be performed as a result of an entry in a programmed time schedule 734. For example, a scheduled event might cause the implantable device 110 to alert the patient to upload data. Other possibilities will be apparent with regard to the PCU 114, the base unit 210, the programmer 216, or the database 222. In particular, routine scheduled entry of a quality of life survey might be scheduled at the PCU 114, the base unit 210, or the programmer 216. The database 222 might perform maintenance or storage management tasks on a particular schedule. Any of the devices according to the invention might perform diagnostics at certain scheduled times. There are, of course, numerous other possibilities.

An action might be performed in response to a message 736 received by the implantable device 110, the PCU 114, the base unit 210, the programmer 216, or the database 222. This feature, in an embodiment of the invention, can be considered a "remote command" capability—one of the network units is commanded to perform an action via the communications network 112 or some other communication link. For example, a command entry at the PCU 114 might cause the implantable device 110 to perform a certain action, such as store a record of EEG data or switch modes—this would be accomplished via a message transmitted from the PCU 114 to the implantable device 110 (and also possibly to the database 222 for record keeping purposes). Many other possibilities will be apparent.

One or more actions can be performed as a result of a calculation 738 performed by the implantable device 110, the PCU 114, the base unit 210, the programmer 216, or the database 222. For example, an evaluation of recently-uploaded EEG data at the programmer 216 or the database 222 might indicate that a patient is particularly susceptible to seizures over a time period in the near future; that calculation in an embodiment of the invention might cause an alert to the patient and/or a message to the patient's physician to be generated automatically. Similarly, a calculation based on patient data uploads or other use of the system might be made at the PCU 114, the base unit 210, or the programmer 216 to determine whether a message should be sent or a physician office visit should be scheduled.

While it is observed above that a number of the communications operations performed in a system according to the invention can be deferred or queued if the communications network 112 is unavailable or should not be used (e.g., wireless communications in a hospital environment), the remaining portion of this specification will assume real-time communications. Numerous possible alternate methods involving deferred or queued communications will be apparent to the reader.

Figure 8:
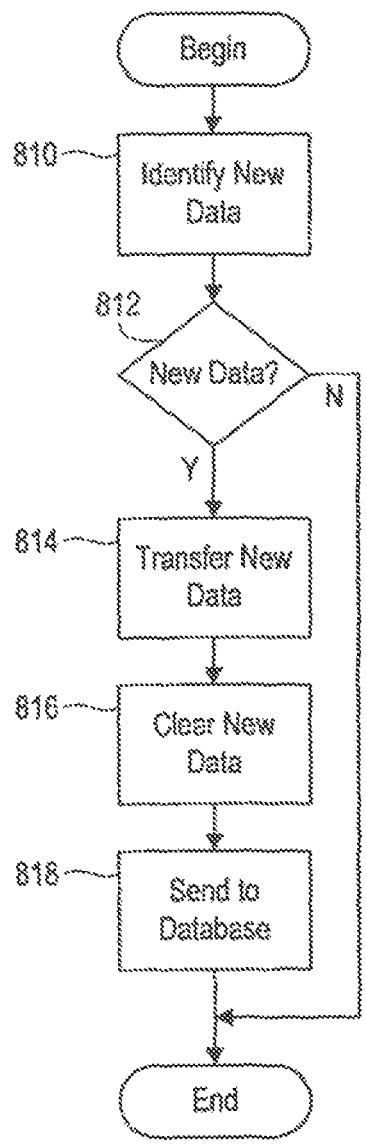
FIG. 8 is a flow chart illustrating an exemplary data upload functional process performed according to the invention.

FIG. 8 illustrates the process performed in uploading data stored by the implantable device 110 to another device according to the system accessible via the communications network 112, such as the PCU 114, the base unit 210, or the programmer 216.

Initially, the implantable device 110 identifies any new data to be uploaded (step 810). If there is any new data for upload (step 812), the new data is transferred (step 814) over a link (such as the wireless link 120) to a target device, such as the PCU 114, the base unit 210, or the programmer 216. Any suitable communications protocol can be used for the link. The new data is then cleared (step 816) after it has been transferred. Optionally, before the data is cleared, a handshaking or confirmation operation between the implantable device 110 and the target device can be used to confirm that the data transfer completed successfully. Alternatively, the new data is not cleared upon every transfer operation according to FIG. 8, but is cleared only upon command from the target device (e.g., after the new data has been successfully stored and reconciled) or upon certain additional operations being performed such as programming (see FIG. 10). The recently transferred new data is then sent on (step 818) to the database 222 for long-term storage. At this stage, optionally, the new data can also be sent to other network units, such as the programmer 216 or a remote programmer 220 to allow it to be analyzed or otherwise used.

If there is no new data for the device 110 to transfer (step 812), then no transfer operation is performed. However, it should be noted that a message to that effect (i.e., no new data) can optionally be sent to one or more network units. See the description of FIG. 16, below.

The same process illustrated in FIG. 8 can also be used to upload information from the PCU 114 or another device on the network 112 that periodically transfers information to the database 222 or elsewhere. In such an embodiment, the operation of clearing data (step 816) might be performed differently under different circumstances—for example, the PCU 214 and the programmer 216 are preferably programmed to retain some information even after a synchronization or transfer operation is performed, such as a summary and log of the transferred data. Accordingly, the specific devices (e.g., the device 110, the PCU 114, and the database 222) are used as exemplary data sources and targets, and others are certainly possible within a system according to the invention.

Figure 9:
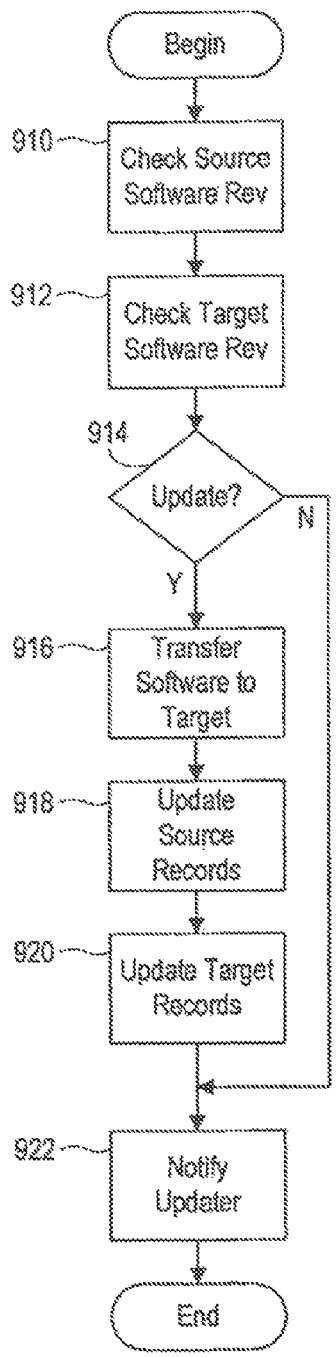
FIG. 9 is a flow chart illustrating an exemplary software download functional process performed according to the invention.

FIG. 9 illustrates the process used in a system according to the invention to download new software and software updates from one device to another. For example, it is contemplated that software updates for the implantable device 110 will reside in the database 222, but typically will be transferred from the database 222 to another network unit (such as the PCU 114 or the programmer 216, to name two) prior to programming the implantable device 110.

The process begins by examining the revision level of the software at the source device, for example the PCU 114 or the programmer 216 (step 910). The revision level of the software at the target device, for example the implantable device 110, is then also checked (step 912). If the target device has an older version of the software, then an update is performed (step 914). The software program is transferred from the source device to the target device (step 916) and installed. The source device's records are then updated to reflect the transfer and installation of the new software (step 918), and the target device's records are also updated accordingly (step 920). The originating updater, for example the database 222, is then notified that the implantable device 110 (or other network unit) has received and is running the latest software update (step 922).

If the target device already has the newest software revision, then no update is performed (step 914) and the originating updater is informed that no update was performed (step 922).

When the upgrade is complete, the target device verifies the integrity of the newly received code (for example, by comparing checksums or performing other diagnostics). In an embodiment of the invention, if the upgrade failed, the old software remains operative, and if the upgrade succeeded, the new software replaces the old. The updating device is notified accordingly (as in step 922), or alternatively, awaits a query from the database 222 or other updating device.

Besides the implantable device 110, it might be desirable to enable other network units according to the invention to receive and accept software updates according to the method set forth in FIG. 9. For example, improved versions of the software operating on the PCU 114 might be provided by the same mechanism. Additional functionality or reliability can also be provided this way for other network units, including the base unit 210 and the programmer 216.

When a new software version is deployed, it is frequently desired to update as many devices as possible within a short period of time. Accordingly, in an embodiment of the invention, the database 222 (or other network unit storing the software update) is enabled to perform a network broadcast or multicast of the software update to many network units (such as PCUs or programmers) simultaneously or substantially simultaneously, with the network units enabled to update the software in their respective implantable devices (i.e., those implantable devices that are directly or indirectly connected) or other target devices. This procedure is preferably performed as automatically as possible. If certain target devices are unaccounted for after time has elapsed, and those devices have not connected to any network unit for an upgrade of the sort described above, then messages can be sent to the patients or caregivers responsible for the not-yet-upgraded target devices. Sending messages will be described in additional detail below with reference to FIG. 16.

As is described in greater detail in U.S. patent application Ser. No. 09/977,052 (referenced above), optimum performance of the implantable device 110 is dependent on the use of patient-specific parameters and other device settings that are generally developed and calculated outside of the device 110. Such sets of parameters and settings are generally referred to, herein and elsewhere, as "templates." In particular, it is contemplated that templates are developed by receiving raw patient-specific data from the implantable device 110 (or other data recording apparatus), by the method illustrated in connection with FIG. 8, above, processing the patient-specific data at the programmer 216 or the database 222, developing a suitable patient-specific parameter set, and then updating the parameter set used by the implantable device 110 by transferring it to the device 110.

Figure 10:
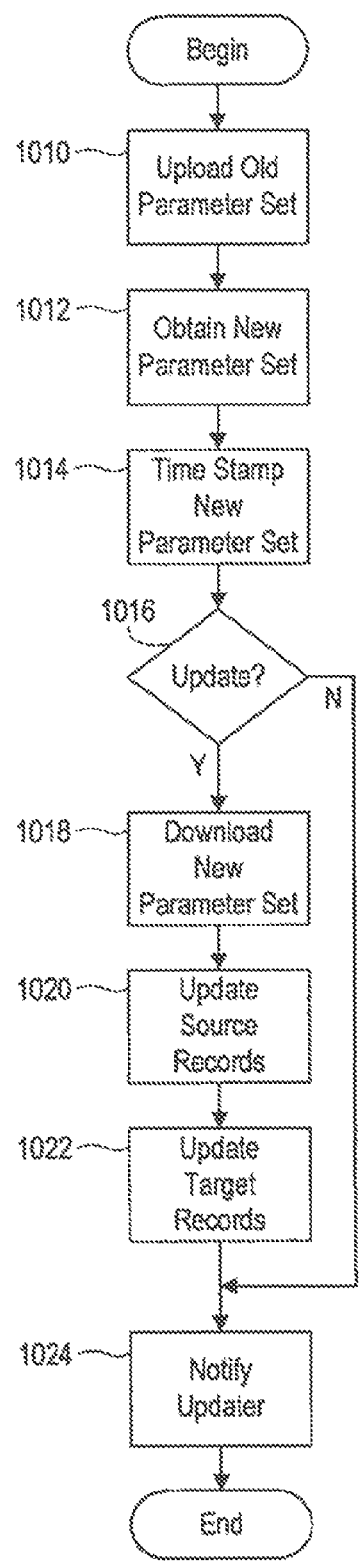
FIG. 10 is a flow chart illustrating an exemplary parameter download functional process performed according to the invention.

An advantageous method for updating templates and parameters in the implantable device is illustrated by the flow chart set forth in FIG. 10. To start the process, the old parameter set is uploaded from the device 110 if necessary or desired (step 1010). This possibility is provided to allow the programmer 216, if it was not the source of the old parameter set (and if it is not possible to access the database 222 to otherwise obtain the old parameter set) to receive the old parameter set and use it as a starting point for modifications. Once modifications are complete or a new parameter set has otherwise been obtained (step 1012), the new parameter step is time-stamped for reference purposes (step 1014) and it is determined whether an update is necessary or desired (step 1016). The decision to update is preferably left to the discretion of the treating clinician.

If an update is desired, the new parameter set is downloaded (step 1018) to the device 110, and if successful, records in the source device (e.g., the programmer 216) and the target device (e.g., the device 110) are updated accordingly (steps 1020 and 1022, respectively). The updating device or other data repository, such as the database 222, is then notified (step 1024) that a new parameter set is in place, or alternatively failure or success messages are sent upon query from the data repository.

Also important to effective seizure and other neurological event detection according to the invention is the ability to annotate data received from the implantable device 110, that is, to correlate the raw data with clinical observations. Such correlated clinical observations can be a tremendous assistance in the development of patient-specific detection parameter sets. Accordingly, as one of the goals of implantable medical devices is to facilitate patient independence, patients having such devices will not always be under direct medical observation. The patients themselves, however, can be a source of information.

In traditional epilepsy care, for example, patients are often provided with a seizure log, essentially a notebook in which to record dates, times, and symptoms of episodes they experience. Although entries made by epilepsy patients are not definitively reliable, such entries can be useful to clinicians in diagnosis, ongoing treatment, medication management, and other applications. And for purposes of parameter set development for the implantable device, seizure log entries serve a more direct purpose. They enable the annotation of EEG data to indicate where seizures occur and where automated detections should be occurring. Although EEG data will still typically be reviewed by a trained epileptologist, seizure log information from the patient can improve the process dramatically by pointing out specific time periods of interest and reducing the (often tremendous) amount of raw data the clinician must examine. See U.S. patent application Ser. No. 09/977,052, referenced above, for additional details.

A system according to the invention is particularly well suited for functionality resembling that of a traditional paper seizure log. A PDA (such as the PCU 114) can be programmed to accept seizure-log-type data from the patient upon command. This kind of functionality is particularly convenient in a portable device, such as the PCU 114, whether implemented in a PDA, mobile telephone, wristwatch, or other form factor.

Figure 11:
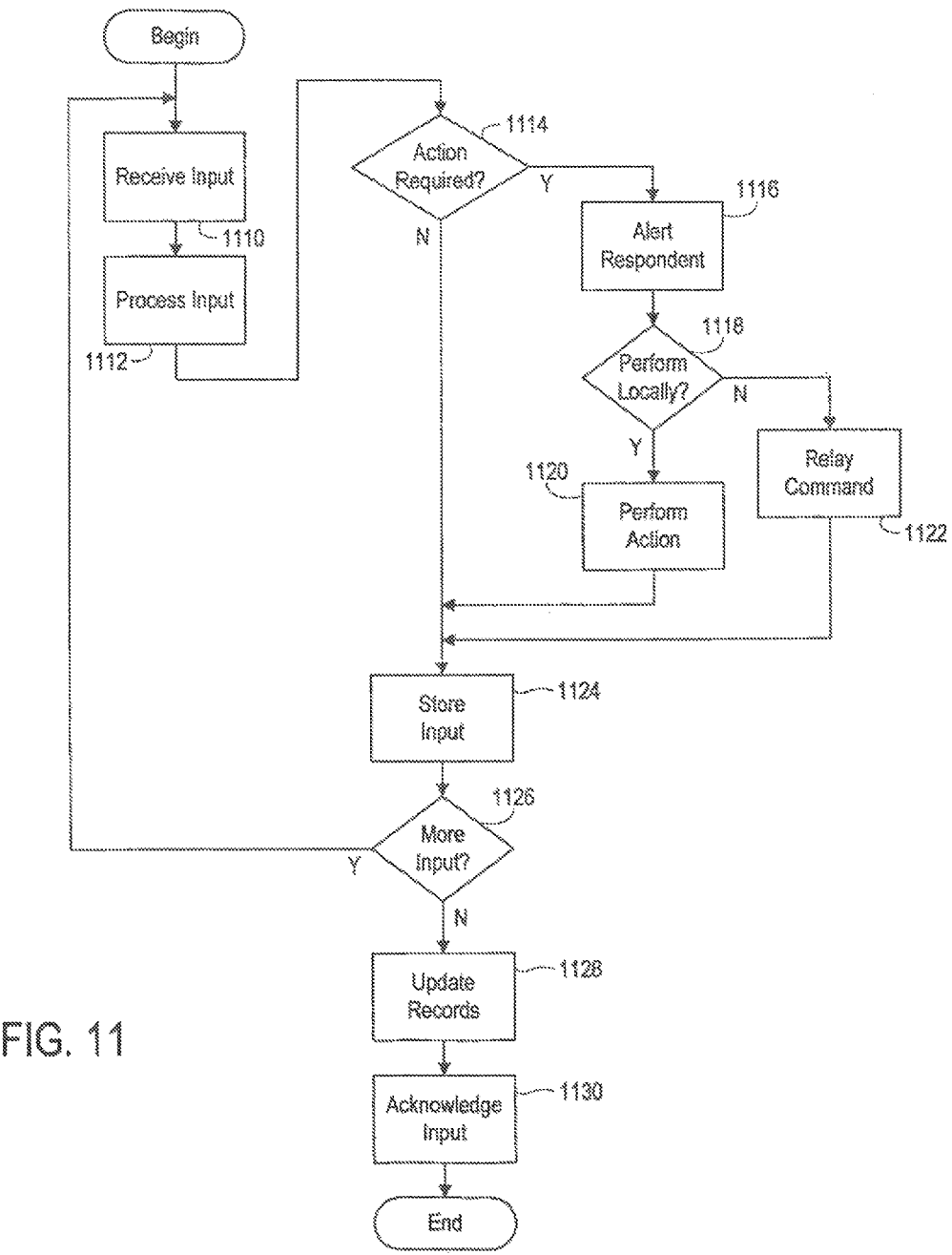
FIG. 11 is a flow chart illustrating an exemplary seizure log entry functional process performed according to the invention.

The flow chart of FIG. 11 sets forth a method for entering and processing a seizure log according to the invention. Initially, after the patient has indicated a desire to enter seizure log information to the PCU 114 (for example, by entering a command 732), the seizure log input is received by the PCU 114 or other apparatus (step 1110). The input is then processed (step 1112) to determine whether any action is necessary (for example, if the entry indicates or suggests that an emergency is occurring or imminent). If an action is required (step 1114), some respondent such as the patient's treating physician is alerted (step 1116, described in greater detail with reference to FIG. 16), and if the desired action can be performed locally (step 1118) by the device receiving the seizure log entry, then the action is performed (step 1120). The desired action can be pre-programmed into the PCU 114, received from a remote location such as the database 222, or directed by a physician or other individual at a remote location (e.g., operating a remote programmer 220 or other device connected to the communications network 112). Examples of possible local actions include providing an audio or visual alert to the patient, providing instructions to the patient, or requesting the input of further information.

If the action cannot be performed locally (step 1118), a command representative of the action is relayed (step 1122) via the communications network 112 to another network unit capable of carrying out the command. For example, the implantable device 110 might be commanded to switch into a different detection mode, apply different types of therapy, delivery an audio or somatosensory warning to the patient, or go inactive. Other devices, such as the programmer 216 or a remote programmer 220 might provide an alert to a physician. Many other options are possible and will be apparent to the reader hereof.

In any event, regardless of whether an action is required (step 1114), the input is stored (step 1124) for later retrieval. If there is more information to be received (step 1126), the PCU 114 will receive and process whatever else is provided by the patient or operator (starting again at step 1110). Otherwise, the records of the PCU 114 are updated (step 1128), and the input is acknowledged (step 1130) to the patient or user.

While the PCU 114 is described above as the apparatus best suited for seizure log entry, it should be noted that the base unit 210, the programmer 216, or any other network unit according to the invention can be provided with the same functionality, for use by the patient, a caregiver, or a clinical professional. In any event, upon upload (FIG. 8), the seizure log and associated information will be transferred to the database 222 and analyzed if necessary.

It is also desirable in some circumstances to be able to administer surveys and examinations to patients and their caregivers. Traditionally, this has required an office visit to allow the survey or exam to be administered under controlled conditions. However, it will be recognized that a system according to the invention affords on opportunity for automated and remote administration of surveys and examinations.

One clinically useful tool is a quality of life ("QOL") survey, which in general is used to determine how well a patient is doing. Several specific QOL surveys are common in epilepsy treatment, including the QOLIE series (Quality Of Life In Epilepsy), which has a short version (QOLIE-10), a medium-length version (QOLIE-31), and a long version (QOLIE-89). For more information on QOLIE-10, see J. A. Cramer et al., "A Brief Questionnaire to Screen for Quality of Life in Epilepsy: The QOLIE-10," Epilepsia 37(6): 577-582 (1996). For details on QOLIE-31, see J. A. Cramer et al., "Development and Cross-Cultural Translations of a 31-Item Quality of Life in Epilepsy Inventory," Epilepsia 39(1): 81-88 (1998); and B. G. Vickrey et al., Quality of Life in Epilepsy QOLIE-31 (version 1.0): Scoring Manual and Patient Inventory, Santa Monica, Calif.: RAND (1993). For more information on QOLIE-89, see O. Devinsky et al., "Development of the Quality of Life in Epilepsy Inventory," Epilepsia 36(11): 1089-1104 (1995); and B. G. Vickrey et al., Quality of Life in Epilepsy QOLIE-89 (version 1.0): Scoring Manual and Patient Inventory, Santa Monica, Calif.: RAND (1993). Other surveys are also available, both epilepsy-specific (e.g., the ESI-55, see B. G. Vickrey et al., "A Health-Related Quality of Life Instrument for Patients Evaluated for Epilepsy Surgery," Med. Care 30: 299-319 (1992) and the Washington Psychosocial Seizure Inventory (WPSI)) and general (e.g., the SF-36 and SF-12 short forms), and ad hoc surveys and questionnaires might be employed to advantage.

It is also advantageous to be able to administer various neuropsychiatric examinations automatically, remotely, or through a system according to the invention. Neuropsychiatric examinations might be useful for epilepsy patients and others being treated with an implantable medical device according to the invention. See, e.g., T. Onuma, "Classification of Psychiatric Symptoms in Patients with Epilepsy," Epilepsia 41(Suppl. 9): 43-48 (2000); F. Lopez-Rodriguez et al., "Personality Disorders Among Medically Refractory Epileptic Patients," J. Neuropsychiatry Clin. Neurosci. 11(4): 464-69 (Fall 1999); and V. M. Neppe et al., "Modern Perspectives on Epilepsy in Relation to Psychiatry: Behavioral Disturbances of Epilepsy," Hosp. Community Psychiatry 39(4): 389-96 (April 1998). One example of a neuropsychiatric examination that might be administered through a system according to the invention is the Screening Cerebral Assessment of Neppe (the "BROCAS SCAN"). See V. Neppe et al., "The Application of the Screening Cerebral Assessment of Neppe (BROCAS SCAN) to a Neuropsychiatric Population," J. Neuropsychiatry Clin. Neurosci. 4(1): 85-94 (Winter 1992). It should be understood that the BROCAS SCAN would advantageously be modified to reduce its reliance on direct clinician-to-patient interactions and subjective analysis of responses; or alternatively, a real-time or deferred link between the patient's PCU 114 and a clinician (at a remote programmer, for example) can be established to permit such interactions and analysis.

Figure 12:
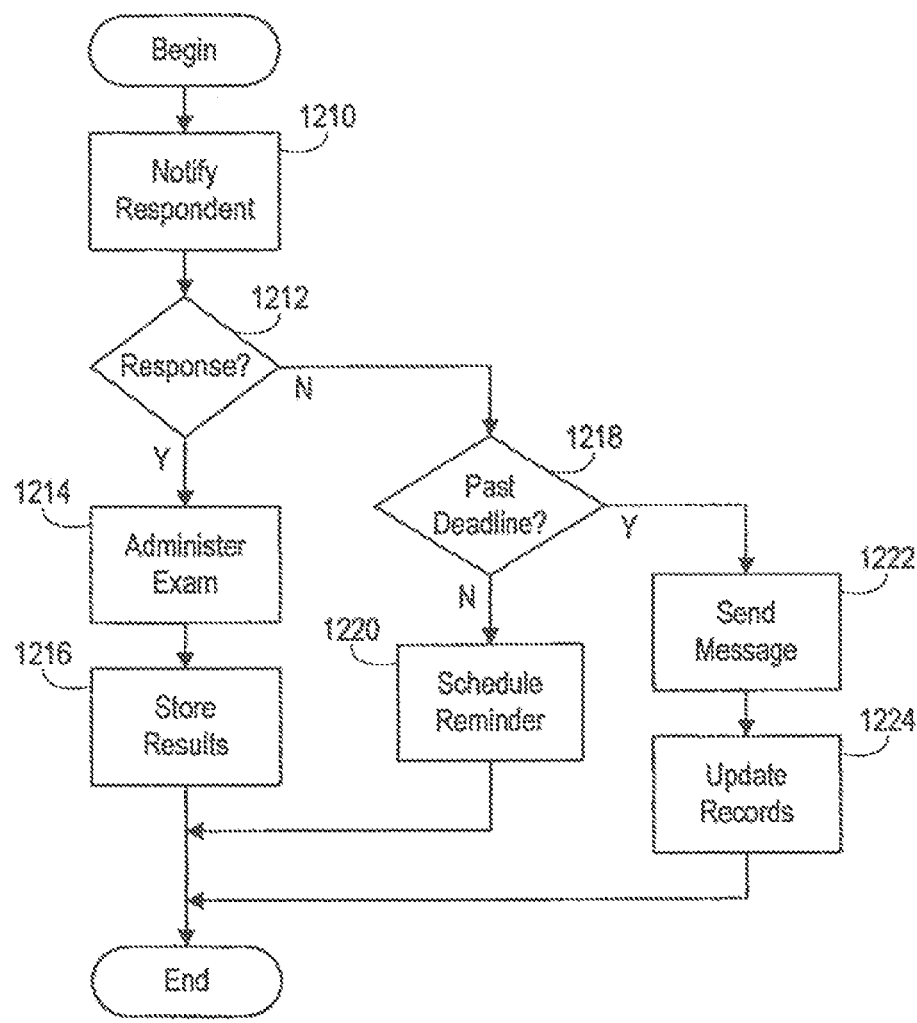
FIG. 12 is a flow chart illustrating an exemplary quality of life survey response functional process performed according to the invention.

An advantageous method for administering a survey or examination is detailed in FIG. 12. Initially, if a survey or exam is administered on a certain schedule 734 (FIG. 7), the patient or user is notified that it is time to respond to the desired survey or examination (step 1210). A quality of life survey might be administered every three months, for example, but other surveys and exams might be sought either more or less frequently. The schedule used may depend on clinical circumstances, for example the nature of the patient's seizure log entries.

If the patient responds to the notification (step 1212), the survey or examination is administered (step 1214) and the results are stored (step 1216) for later retrieval. Optionally, the results can immediately be transmitted to another location, such as one of the remote programmers 220 or the database 222. If the patient does not respond (step 1212), a deadline for response is checked (step 1218), and a patient reminder is scheduled (step 1220) if the deadline has not yet passed. If the deadline has passed or is imminent (step 1218), a message is sent (step 1222) to an appropriate individual or location (such as the treating physician or clinic) and records are updated (step 1224). In response, the treating physician can take whatever action is clinically indicated, such as rescheduling the survey or examination, or alternatively summoning the patient in for an office visit (e.g., via the message mechanism of the invention described with reference to FIG. 17). Upon upload (FIG. 8), the survey or examination results will be transferred to the database 222 and analyzed if necessary.

Many of the operations performed by an interactive system according to the invention are initiated by way of a command 732 (FIG. 7) entered at one of the network units. As the term is used herein, a command can refer to a specific directive to perform an action, or can be a direct or indirect consequence of any user-initiated action, such as entering data, pushing a button, speaking a phrase into the microphone 138 (FIG. 1), docking the PCU 114 into the docking station 128, etc. A command can be initiated or received at any of the network units described herein, including the implantable device 110 (e.g., by using a magnet or other interaction device), the PCU 114, the base unit 210 or the mobile base unit 214, the programmer 216, the personal computer 218, or one of the remote programmers 220. There are numerous other possibilities, any of which can constitute a command according to the invention.

Figure 13:
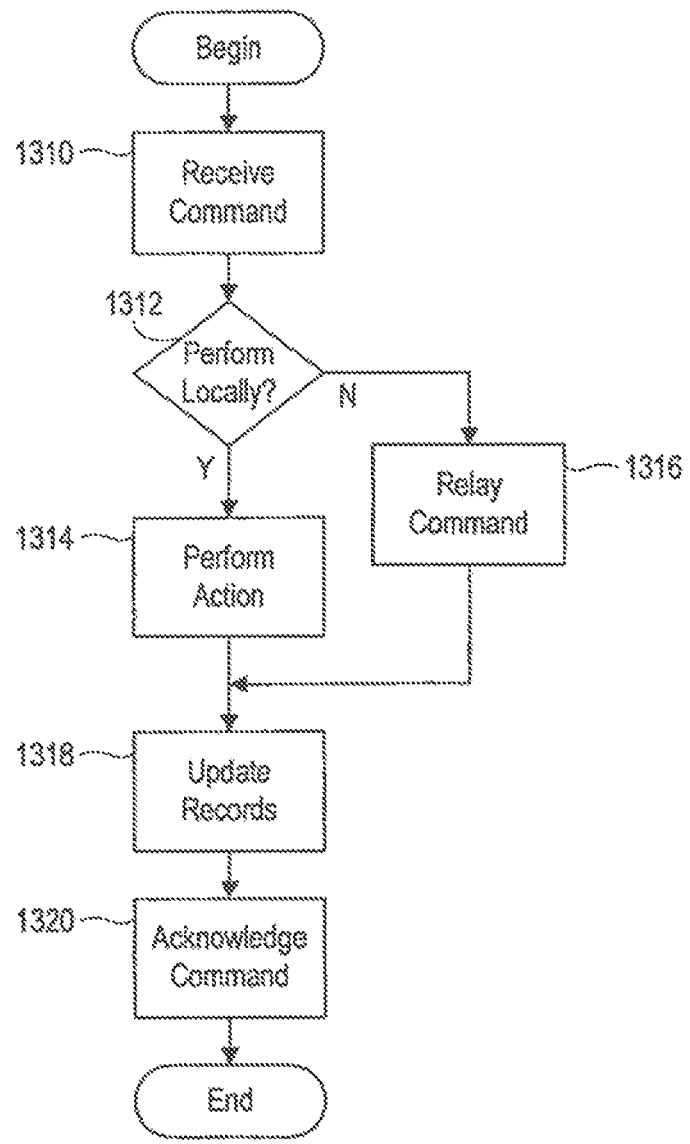
FIG. 13 is a flow chart illustrating an exemplary generic command entry functional process performed according to the invention.

A command can be processed according to the method illustrated in FIG. 13. Initially, the command is received by a device (step 1310), which for the illustrative example provided here shall be the PCU 114. If the command can be executed locally (step 1312), the corresponding action is performed (step 1314). As described herein, there are many possible and desirable actions, including sending messages, storing information, changing modes, etc. If the command cannot be executed locally (step 1312), it is relayed to the network unit capable of performing the desired action (step 1316). The system's records are then updated (step 1318) to reflect the command and any action performed, and the command is acknowledged to the user (step 1320).

It may be necessary in the operation of a system according to the invention to alert a user (such as a patient, caregiver, or physician) to a condition or event that requires urgent attention. The flow chart of FIG. 14 provides an exemplary method for receiving and handling such alerts.

When an alert is received (step 1410) at any network unit, typically from the communications network 112, the implantable device 110, or some other communications channel, it is immediately processed (step 1412) to determine what actions are required. If the alert can be delivered locally (step 1414) to the user, the alert is immediately delivered (step 1416). In general, an alert can be an audio, visual, or somatosensory warning, a message, or some other form of communications. If the alert cannot be delivered locally (step 1414), it is relayed (step 1418) to the destination network unit.

If the alert requires a response (step 1420), the response is awaited (step 1422) for a desired period of time, either preset or programmed. If a response is received (step 1424), it is stored (step 1426) for later retrieval or immediate transmission as a message (see FIG. 16). The system's records are then updated (step 1432) to reflect successful delivery of the alert, regardless of whether a response was required. If no response is received (step 1424), a message is sent (step 1428; see FIG. 16) to a physician, caregiver or other individual capable of following up on the alert. The destination of the message may depend on the nature of the alert. The system's records are then updated (step 1430) to reflect the successful delivery of the alert and the user's failure to respond.

Figure 14:
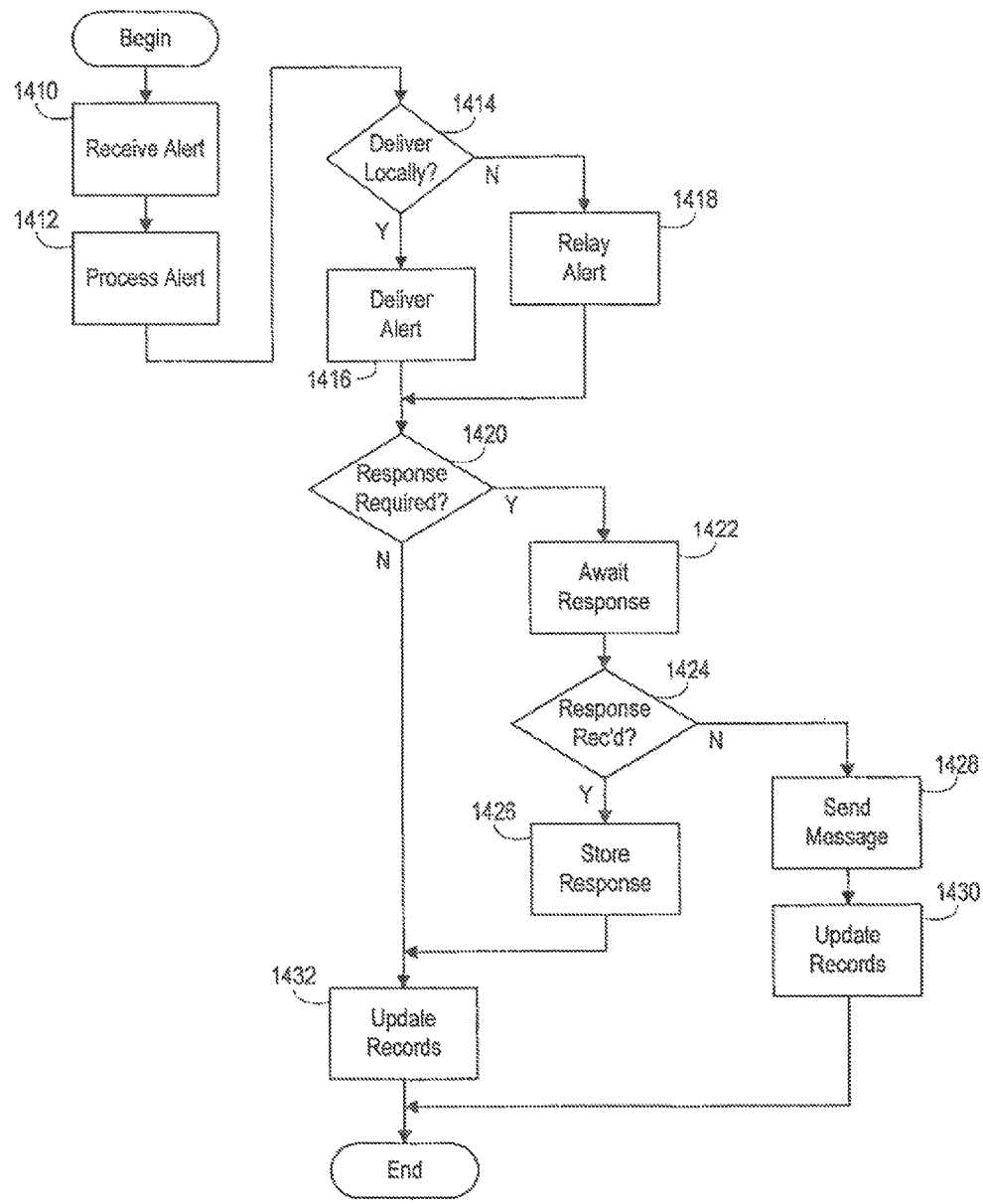
FIG. 14 is a flow chart illustrating an exemplary user alert functional process performed according to the invention.

An alert provided according to the method illustrated in FIG. 14 can be provided to the patient (preferably via the implantable device 110 or the PCU 114) if the patient is in the best situation to respond to the alert, or to a caregiver (preferably via the PCU 114 or the base unit 210) if the caregiver is best situated. It is also contemplated that in certain circumstances an alert can be provided to both the patient and a caregiver. Depending on the recipient's role, the information provided by the alert may differ. For example, a patient might be instructed simply to seek immediate care, while a caregiver might be given more detailed instructions on how to handle the urgent condition the alert pertains to. The different levels of information may be preset and dependent only on the recipient's general role, patient or caregiver, or may be individually programmed depending on the circumstances and the clinical needs of different patients.

Figure 15:
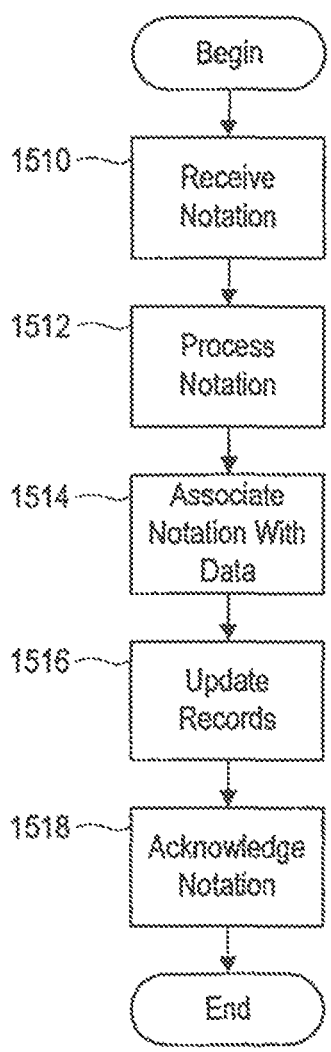
FIG. 15 is a flow chart illustrating an exemplary text note entry functional process performed according to the invention.

FIG. 15 illustrates an exemplary method used to associate notes and other data entries with data recorded by the implantable device. This functionality can be used by the patient to enter notes that correspond to stored EEG data (although the seizure log of FIG. 11 can be used similarly), or simply to explain circumstances that might correspond to other measurements or data items stored by the implantable device 110, PCU 114, or other apparatus according to the invention. Initially, the patient or other user enters a notation (step 1510), which is received by the device being used (typically the PCU 114). The notation is then processed (step 1512), e.g., by compressing it if necessary and assigning it a date and time stamp. The notation is then associated and stored with any desired data (step 1514), for example stored EEG records, diagnostic information, seizure log entries, QOL survey entries, etc.—the data to associate the notation with can preferably be selected by the user, or by default, can be given a date and time stamp and simply stored with all data. The system's records are then updated to reflect the notation (step 1516), and the entry of the notation is acknowledged to the user (step 1518). In an embodiment of the invention, any notations entered via the method specified in FIG. 15 are uploaded with other data according to the flow chart of FIG. 8.

Figure 16:
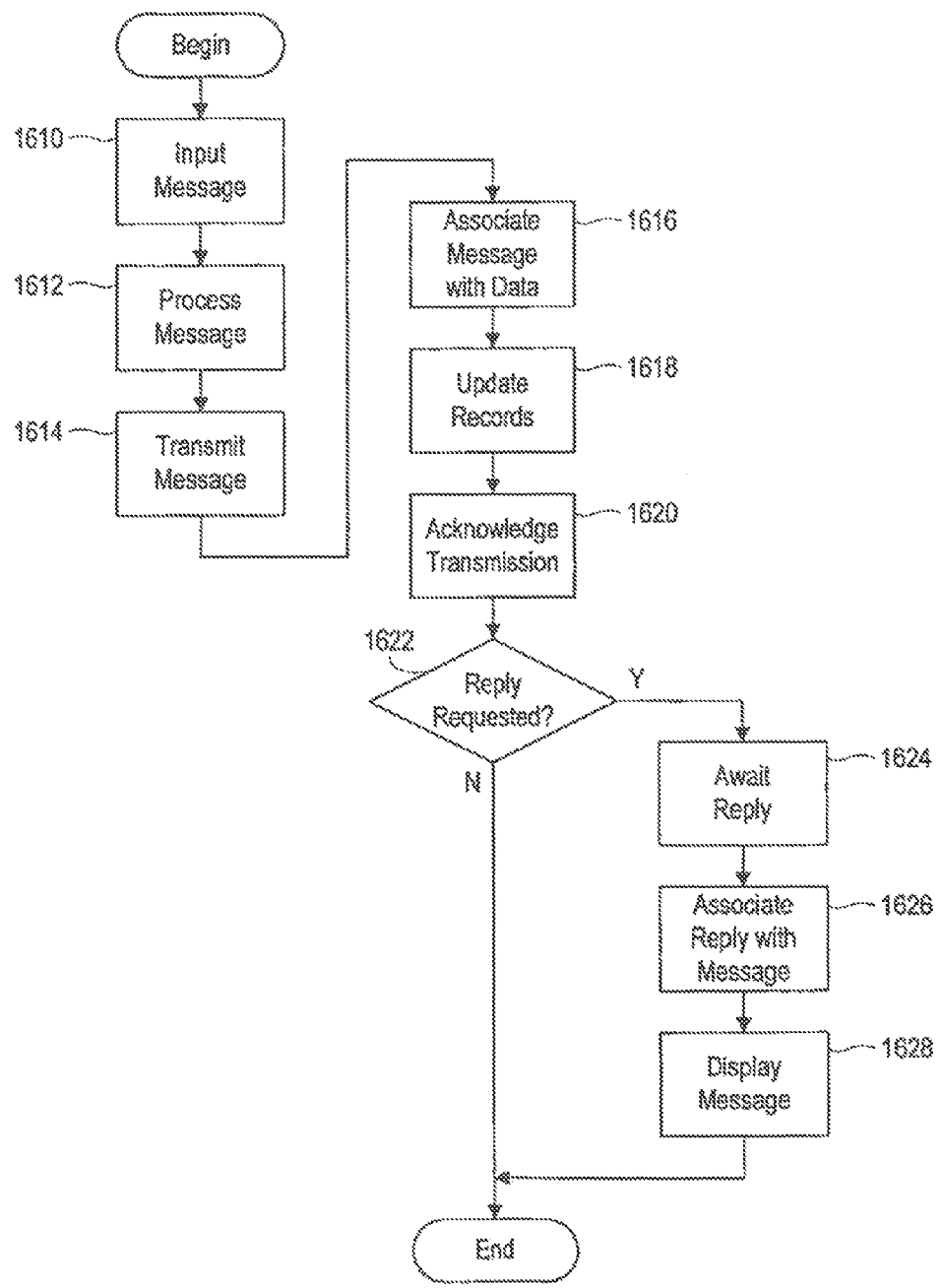
FIG. 16 is a flow chart illustrating an exemplary message sending functional process performed according to the invention.

As referenced above, FIG. 16 depicts an illustrative method for sending messages from one apparatus to another in a system according to the invention. A message (text, audio, image, or any other format) is input by a user (step 1610) and received by the sending device. Typically, in a system according to the invention, the sending device will be the PCU 114, the base unit 210 or mobile base unit 214, the programmer 216, or the personal computer 218. The message is then processed (step 1612) to identify its urgency and destination and to package the message for transmission.

In an embodiment of the invention, the sending device is adapted to encrypt the message while processing it (step 1612), thereby enabling commercial transactions involving financial data and the like. For example, if the patient is alerted that a certain medication change is necessary, the user would be able to send an encrypted message (with credit card or insurance coverage information) to a nearby pharmacy to have the prescription filled and paid for. It should be noted that encryption is useful in a broad array of contexts within a system according to the invention, and in an embodiment of the invention, essentially all communications across the communications network 112 or via wireless links will be encrypted to preserve the patient's privacy and security. It should be noted that certain communications protocols, such as the IEEE 802.11b protocol for wireless communications, include encryption; a system according to the invention can either employ the provided encryption or alternatively specifically encrypt the data (potentially enabling even greater security), depending on the needs of the system.

The message is transmitted to its destination (step 1614), either directly or indirectly, typically via the communications network 112, although shorter-range communications links may be used for local devices.

If necessary, the message is associated with any data it might be relevant to (step 1616; see also FIG. 15), and system records are updated accordingly to reflect the transmitted message (step 1618). Successful transmission of the message is then acknowledged to the user (step 1620).

If a reply to the message was requested (step 1622), a reply is awaited for a time period that can be either preset or programmed (step 1624). When a reply is received, it is associated in device storage with the original message (step 1626) and displayed to the user (step 1628).

It should be noted that in an embodiment of the invention, traditional Internet e-mail can also be used to send messages (FIG. 16) and alerts (FIG. 14) to patients and other individuals; such communications need not be transmitted over the infrastructure established by the invention.

Figure 17:
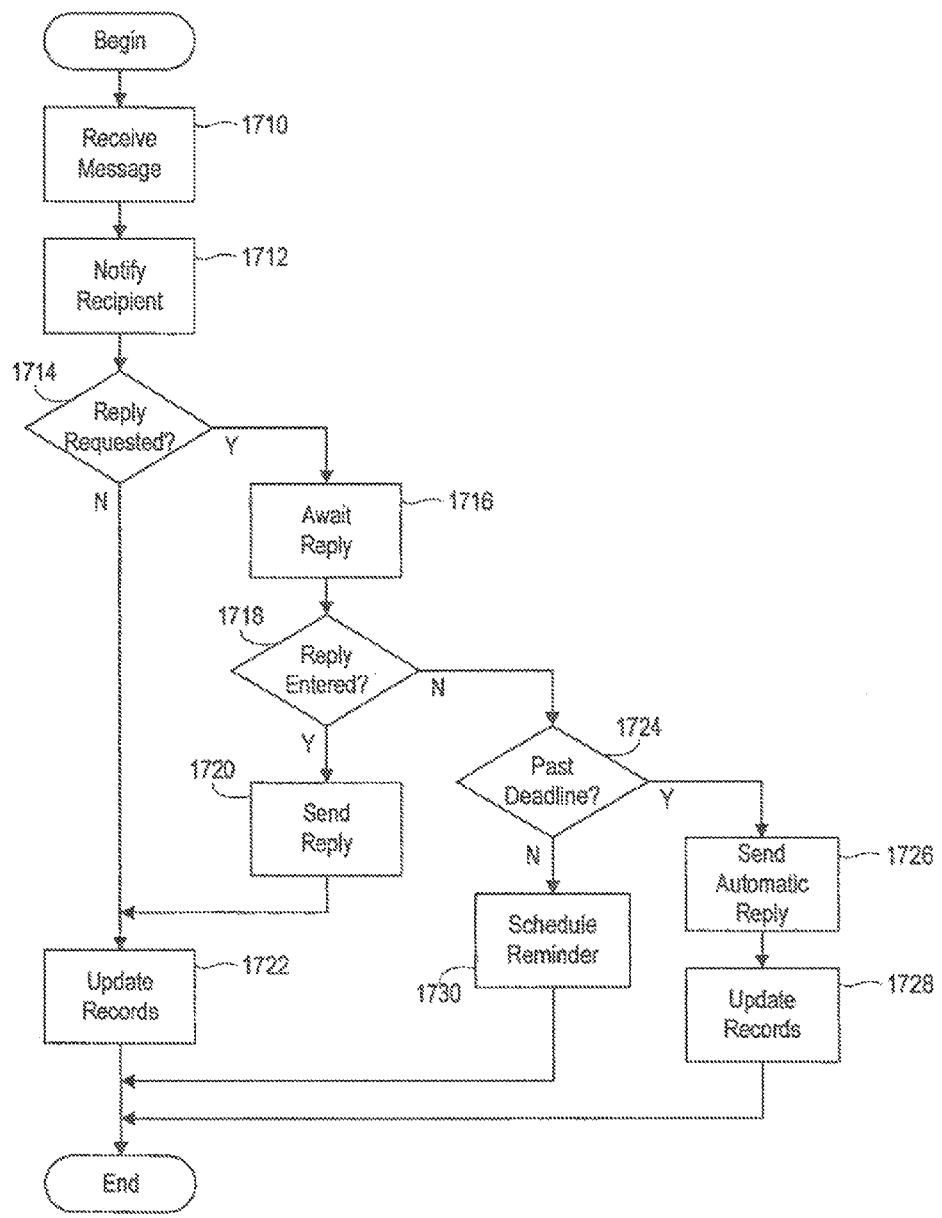
FIG. 17 is a flow chart illustrating an exemplary message receiving functional process performed according to the invention.

The technique used to process received messages is illustrated by the flow chart of FIG. 17. When a message is received (step 1710) from the communications network 112 or some other source, such as a local device, the recipient is immediately notified (step 1712). If a reply was requested (step 1714), entry of the reply is awaited (step 1716) for a preset or programmable time period. If a reply is entered (step 1718), it is transmitted back to the original message sender (step 1720), and system records are updated to reflect the message and the reply (step 1722). If no reply was requested, the records are updated (step 1722) to reflect only the original message.

If a reply was requested (step 1714) and no reply was entered (step 1718), it is determined whether a deadline has passed (step 1724). If the deadline has passed, an automatic reply is sent (step 1726) and the system's records are updated accordingly (step 1728). The original message sender may then decide how to follow up on the failure to reply. If the deadline has not passed (step 1724), a reply reminder is simply scheduled (step 1730). It should be noted that the reply reminder, like other scheduled events handled according to the invention, causes an action to be performed at a certain time according to the specified schedule 734 (FIG. 7). Accordingly, at the proper time, the scheduled event is treated essentially as a command according to the method of FIG. 13, and can be performed locally or remotely, depending on the circumstances.

Particularly in initial patient care for the treatment of epilepsy and other neurological disorders, it is useful to be able to monitor a patient's condition in substantially real time. This can be performed by an invasive surgical process to implant monitoring electrodes within the patient's cranium, and can also be performed non-invasively with scalp electrodes (which tend to have some disadvantages in comparison to implanted electrodes). However, it will be recognized that if an implantable device 110 is already implanted in the patient and receiving data from implanted electrodes, it is far preferable to be able to monitor that data instead of using either of the alternate approaches.

Figure 18:
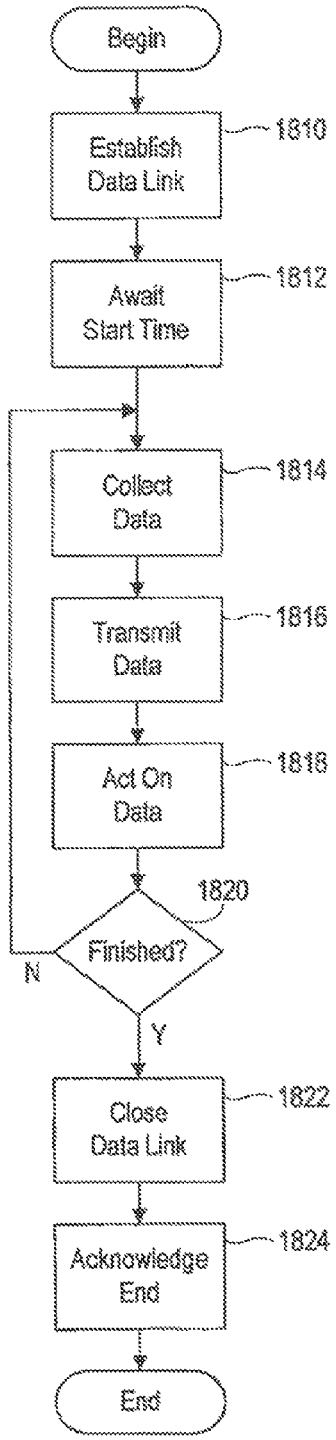
FIG. 18 is a flow chart illustrating an exemplary continuous monitoring functional process performed according to the invention.

Accordingly, FIG. 18 represents a method for performing real-time monitoring of patient condition (including real-time EEG monitoring) according to the invention. As described above, the implantable device includes a number of electrodes, an electronics package capable of translating the EEG signals received by the electrodes into digital data, and a communications capability. The method of FIG. 18 uses those capabilities for real-time monitoring.

Initially, a data link is established between the implantable device 110 and the apparatus being used for monitoring (step 1810). Generally, the monitoring apparatus will be the programmer 216 or one of the remote programmers 220. If a remote device is used, an indirect communications link may be necessary through a local device (such as the PCU 114 or the base unit 210) and the communications network 112; other aspects of the method operate in the same way.

Upon a specified, programmed, or commanded start time (step 1812), the implantable device 110 collects some data (step 1814) and transmits it in a relatively small packet or short stream to the monitoring apparatus (step 1816). The monitoring apparatus then acts on the data, e.g., by decompressing it, displaying it as a real-time EEG waveform, and storing it. If the real-time monitoring is finished (step 1820), then the data link is closed (step 1822) and the end of monitoring is acknowledged (step 1824) to the patient and the user of the monitoring apparatus (e.g., by a message handled according to FIG. 16 or by some other mechanism). If the monitoring is to continue (step 1820), then the data collection, transmission, and action steps (1814-1818) are repeated as long as desired. It should be observed, of course, that real-time monitoring can be performed only while a communications link is open between the implantable device 110 and other devices. Accordingly, when short-range wireless links are employed, it may be necessary to keep the wand 428 in close proximity to the implantable device 110 for a substantial amount of time.

To ensure a system according to the invention is operating properly, it is necessary to be able to perform diagnostics. And in an interactive system according to the invention, it is advantageous to be able to ensure abnormal diagnostic results are sent to and reviewed by the individuals who most need to see them. A method for accomplishing this is illustrated in FIG. 19.

To start the method, a diagnostic test is performed (step 1910) upon command, schedule, or automatically identified need. If the outcome of the test is abnormal (step 1912), and the user needs to be alerted (step 1914), then an alert is provided to the user (step 1916) according to the method described above with reference to FIG. 14. Even if the user does not need to be alerted (step 1914), there may be a need to alert others (step 1918), such as a caregiver, physician, and in the case of a malfunction, the device's responsible technical and clinical personnel. If so, an alert is sent to an appropriate one of these individuals (step 1920), and if still others need to be alerted (step 1922), additional alerts are sent (step 1920) as necessary. These third-party alerts can be sent as urgent messages according to the method of FIG. 16, for example.

Once the user and any others have been alerted, the device failing diagnostics attempts to respond (step 1924) and correct the situation. Various actions can be taken here that would depend on the clinical and technical circumstances; however, as a fail-safe, the implantable device 110 (or other apparatus failing diagnostic testing) can be put into an inactive or passive monitoring state until further testing, possibly at a physician's office or other medical facility, can be performed. In any event, system records are updated (step 1926) to reflect the failed diagnostic test, any alerts sent, and any actions performed to attempt to rectify the situation.

In an alternative embodiment of the invention, the device performing diagnostics need not "know" that a diagnostic test has failed. In this embodiment of the invention, diagnostics results are transmitted to a processing device (such as the programmer 216 or the database 222) via a message (see FIG. 16) or data upload (FIG. 8); the processing device then evaluates the results and initiates any alerts or corrective measures necessary.

It should be noted that the method described above for performing diagnostics applies equally to any of the devices used in a system according to the invention, including the implantable device 110, the PCU 114, the base unit 210, the mobile base unit 214, the programmer 216 (or one of the remote programmers 220), the personal computer 218, or the database 222.

A patient or user having access to the PCU 114 or other network units according to the invention may have a need to access certain informational records from time to time. For example, a patient while traveling might have an urgent need to identify a nearby physician who has one of the remote programmers 220. The patient might also desire to review a user's guide or other documentation relevant to the implantable device 110 or the system. The volume of information preferably made available to a patient or other user might exceed the amount of storage practically available on the PCU 114 or other accessible device, or may be updated from time to time. Accordingly, there is a need for functionality enabling access to a wide variety of informational materials, regardless of where they may be located in a system according to the invention.

It should further be observed that a physician or other clinical professional using the programmer 216 or another apparatus may have analogous needs—e.g., to identify other nearby clinical professionals and facilities, to access instructions or updated documentation, or to access a new patient's medical history. A query processing capability is provided by a system according to the invention and will be described with reference to FIG. 20.

Initially, query input is accepted from the user (step 2010). This can be accomplished via a navigable menu tree presented on a display, various drop-down lists of preset query choices, or free-form text entry, as desired. If the query can be handled locally (step 2012), e.g., if a physician query is entered into the PCU 114, and a list of physicians is maintained on the PCU 114, then the query is processed (step 2014) and interpreted, and the local data repository is accessed (step 2016) to find a response. A report representing the results (e.g., one or more matching records from the repository) is then generated (step 2018). It will be recognized that it may be necessary to update the contents of the local data repository from time to time; this can be accomplished by a method analogous to the software download described with reference to FIG. 9—the contents of the data repository can be considered a type of software module that needs to be updated periodically, and such an update can be scheduled or commanded as desired.

If the query cannot be handled locally (step 2012), the query is transmitted (step 2020) to the database 222 or another location where it can be handled. Results are generated at the remote location while the queried apparatus awaits receipt of the results (step 2022).

Upon receipt from a remote location (step 2022), or upon local generation (step 2018), the results are presented to the user (step 2024) by visual display, audio code or speech synthesis, or any other suitable means (including the message transmission operation of FIG. 16).

Figure 21:
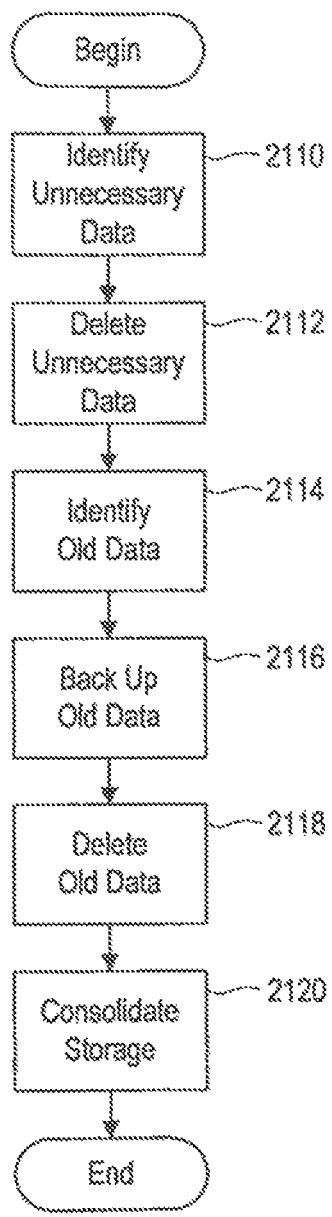
FIG. 21 is a flow chart illustrating an exemplary storage management and housekeeping functional process performed according to the invention.

A basic device housekeeping method consistent with the invention is illustrated by the flow chart of FIG. 21. Because a substantial amount of data is stored, transferred, processed, and manipulated in a system according to the invention, there may be, from time to time, old or superseded data that should be discarded or backed up to keep the system operating at maximum efficiency. The process described herein can be applied to one or more network units (such as the implantable device 110, the PCU 114, the base unit 210, the mobile base unit 214, the programmer 216 or remote programmers 220, the personal computer 218, or the database 222), individually or in a coordinated effort.

The process begins by identifying any unnecessary data (step 2110) in a device according to the invention. The unnecessary data, which is typically described as that data which is not necessary for any purpose whatsoever, is deleted (step 2112). Any old data, not referenced recently or unlikely to be used, is then identified (step 2114) and backed up (step 2116), typically on the database 222. The original copy of the old data is then deleted (step 2118). The backup copy of the old data is still available if it is needed. Storage, including both short-term memory and long-term archival, is consolidated and organized (step 2120), preferably keeping like data together and maximizing contiguous free space.

As illustrated in FIG. 7, the performance of certain actions according to the invention first requires authentication of a user (step 716) or a device serving as the action's source (step 718). Such user authentication is preferably performed in accordance with the methods described below and with reference to FIG. 22; device authentication is analogous and will be described in further detail below.

The process begins by identifying a user (step 2210). In general, this is accomplished by providing an identification data item to an authentication server, which may be on the local device, the database 222, or elsewhere connected to the communications network 112. Examples of identification data items include user login names, numeric codes representative of the user's identity, and biometric information; there are numerous other possibilities.

If the user has already authenticated to the system (step 2212), and too much time has not yet elapsed (step 2214), the desired transaction is allowed (step 2216). The preset or programmable time limit exists to allow consecutive (and nearly consecutive) transactions to be performed without the need to perform detailed authentication for each one, relieving some burden on the system. This approach is well known.

If the user has not yet authenticated (step 2212) or if too much time has elapsed (step 2214), then an authentication input is awaited from the user (step 2218). An authentication input according to the invention can be a password, a device-generated code, one or more items of biometric information, or any of various other known items. Once received, the authentication input is tested (step 2220) by the authentication server. If it is good (step 2222), and the user identification and user authentication information match properly, then the transaction is allowed (step 2216). If not, and one or more retries are allowed (step 2224), then authentication input is again awaited (step 2218) and the process continues. If no retries are available (step 2224), then a failure message is sent (step 2226) to one or more responsible individuals (for example, the patient, the patient's physician, and a system administrator) or a failed access attempt is simply logged, and the transaction is denied (step 2228).

Figure 23:
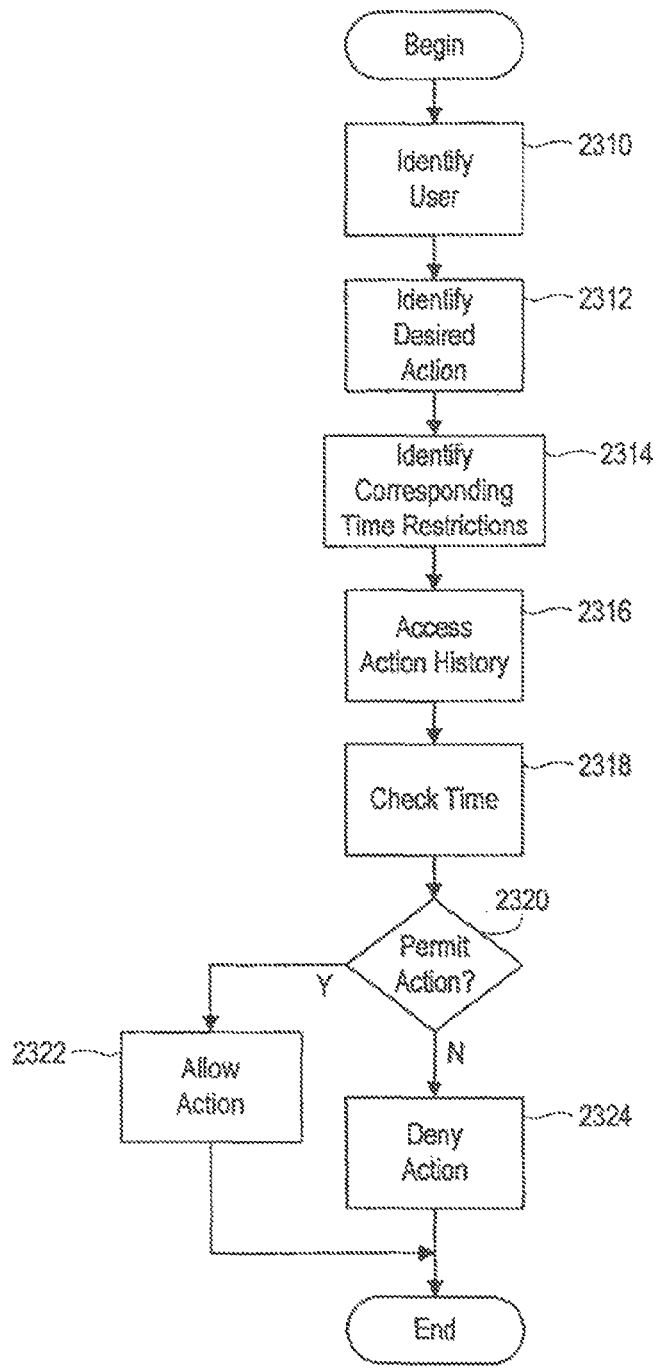
FIG. 23 is a flow chart illustrating an exemplary compulsive use rejection functional process performed according to the invention.

Finally, a method for ensuring patients and other users do not overuse the interactive functionality of a system according to the invention is presented in FIG. 23. It has been observed that certain patients with programmable implantable medical devices tend to use interaction devices more often than recommended. This may lead to accelerated battery depletion, inefficient system usage, and may make other unnecessary demands on the system. The control method provided by the system and illustrated in FIG. 23 will reduce this tendency by limiting access to reasonable intervals.

To start, the system identifies the user making a request (step 2310) and further identifies the nature of the action being requested (step 2312). For example, a given user may tend to try to upload stored data very frequently, e.g., approximately every half hour while awake. Accordingly, after the user and the desired action have been identified, the system identifies a time restriction that corresponds to both the user and the desired action (step 2314). Some users who use the system appropriately might have no time restrictions, while others might have multiple restrictions applying to multiple actions. The time restrictions used by the system can be preset, programmed, commanded (e.g., by a physician), or dynamically and automatically generated and updated by the system based on past behavior.

Once the appropriate time restriction has been identified, the user's history of interaction with the system, including the most recent action of the same type requested by the user, is accessed (step 2316) and its time is determined. The current time is checked (step 2316) and compared to the time of the most recent action of the same type. If the time restriction is met (step 2320), the action is permitted (step 2322) and recorded by the system. Otherwise, permission to perform the action is denied (step 2324).

It should be recognized, of course, that certain actions performed by the system should never be restricted—for example, patients should always be allowed to send urgent messages (see FIG. 16) or make a seizure log entry (see FIG. 11), and if an urgent message is to be sent, it should be possible for the patient to upload and transmit a corresponding EEG record for analysis (see FIG. 8). The system (and the PCU 114 or the implantable device 110) may not always be able to automatically identify an urgent patient care situation or an emergency, so the patient must be given an opportunity to react to perceived emergencies and seek appropriate care through the use of the system.

It should be observed that while the foregoing detailed description of various embodiments of the present invention is set forth in some detail, the invention is not limited to those details and a system according to the invention incorporating an implantable medical device can differ from the disclosed embodiments in numerous ways. In particular, it will be appreciated that embodiments of the present invention may be employed in many different applications to monitor, communicate with, or control a medical device system. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

The invention claimed is:

1. A medical system comprising:
a device adapted to be implanted in a human patient, and configured to: sense signals from the patient, translate the sensed signals into data, store the data in a memory, and transmit the data over a wireless communication interface; and
an apparatus adapted to remain external of the patient, and configured to establish the wireless communication interface with the implanted device, receive a request from the implanted device to allow an action to occur, determine if the implanted device is already authenticated, allow the action when the implanted device is already authenticated and an elapsed time requirement is met, and deny the action until the implanted device becomes authenticated.

2. The system of claim 1, wherein the external apparatus is configured to allow one or more authentication retries when the implanted device is not already authenticated or the elapsed time requirement is not met.

3. The system of claim 1, wherein:
the implanted device is configured to generate an authentication code and transmit the code to the external apparatus; and
the external apparatus is configured to authenticate the source device based on the code.

4. The system of claim 1, wherein the external apparatus is configured to authenticate the source device based on biometric information of the patient.

5. The system of claim 1, wherein the action comprises uploading stored data from the implanted device to the external apparatus and the implanted device is configured to clear the data from the memory upon one of: transmission of the data to the external apparatus, upon confirmation from the external apparatus that the data has been successfully received, or upon receipt of a clear command from the external apparatus.

6. The system of claim 1, wherein the implanted device is configured to store software code in the memory, the action comprises downloading new software code from the external apparatus to replace old software code in the implanted device, and the implanted device is configured to verify integrity of the downloaded new software code, maintain the old software code operative if the new software code is not verified, and replace the old software code with the new software code if the new software code is verified.

7. The system of claim 1, wherein the implanted device is configured to store a parameter set in the memory, and the action comprises downloading a new parameter set from the external apparatus to replace an old parameter set in the implanted device, and the implanted device is configured to verify successful download of the new parameter set, and notifying the external apparatus that a new parameter set is in place if the download is successful.

8. The system of claim 1, wherein the action comprises real-time monitoring of signals sensed by the implanted device, and the implanted device is configured to collect data corresponding to sensed signals, compress the data and transmit the compressed data to the external apparatus, and the external apparatus is configured to decompress the data, display it as a real-time data and store the data.

9. The system of claim 1, wherein the implanted device comprises a neurostimulator.

10. The system of claim 1, wherein the external apparatus comprises one of a database, a programmer, a base unit or a personal control unit.

11. A method for monitoring a condition of the patient with an implanted device and an external apparatus, said method comprising:
establishing a communications link between the implanted device and the external apparatus;
receiving, by the external apparatus, a request to allow an action to occur;
determining, by the external apparatus, if the implanted device is already authenticated;
allowing, by the external apparatus, the action when the implanted device is already authenticated and an elapsed time requirement is met; and
denying the action, by the external apparatus, until the implanted device becomes authenticated.

12. A medical system comprising:
- a device adapted to be implanted in a human patient, and configured to communicate over a wireless communication interface; and
- an apparatus adapted to remain external of the patient, and configured to establish the communication interface with the implanted device, receive a request from the implanted device to allow an action to occur, allow the action to occur when a time restriction related to a past request to perform the action is met, and deny the action when the time restriction related to a past request to perform the action is not met.

13. The system of claim 12, wherein the time restriction is based on a frequency of past requests to perform the action and the nature of the action.

14. The system of claim 12, wherein the time restriction comprises a restriction time period, and the external apparatus is configured to determine if the time restriction is met by being further configured to:
- determine a difference between a current time corresponding to the time of the request to perform the action, and a past time corresponding to the time of the most recent past request to perform the action;
- wherein the time restriction is determined to be met when the difference is at least equal to the restriction time period, and not to be met when the difference is less than the restriction time period.

15. A method for monitoring a condition of the patient with an implantable device and an external apparatus, comprising:
- establishing a communications link between an implanted device and an external apparatus;
- receiving, by the external apparatus, a request from the implanted device to allow an action to occur, the action having a time restriction related to a past request to perform the action;
- allowing the action to occur, by the external apparatus, when the time restriction related to a past request to perform the action is met; and
- denying the action, by the external apparatus, when the time restriction related to a past request to perform the action is not met.

16. The method of claim 15, wherein the time restriction is based on a frequency of past requests to perform the action and the nature of the action.

17. The method of claim 15, wherein the time restriction comprises a restriction time period, and further comprising
- determining, by the external apparatus, a difference between a current time corresponding to the time of the request to perform the action, and a past time corresponding to the time of the most recent past request to perform the action;
- wherein the time restriction is determined to be met when the difference is at least equal to the restriction time period, and not to be met when the difference is less than the restriction time period.

* * * * *